United States Patent
Murphy et al.

(10) Patent No.: US 12,019,133 B2
(45) Date of Patent: Jun. 25, 2024

(54) SYSTEMS, METHODS, AND MEDIA FOR ESTIMATING A MECHANICAL PROPERTY BASED ON A TRANSFORMATION OF MAGNETIC RESONANCE ELASTOGRAPHY DATA USING A TRAINED ARTIFICIAL NEURAL NETWORK

(71) Applicant: Mayo Foundation for Medical Education and Research, Rochester, MN (US)

(72) Inventors: Matthew C. Murphy, Rochester, MN (US); Joshua D. Trzasko, Rochester, MN (US); Richard L. Ehman, Rochester, MN (US); John Huston, III, Rochester, MN (US); Armando Manduca, Rochester, MN (US); Jonathan M. Scott, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 74 days.

(21) Appl. No.: 17/796,431

(22) PCT Filed: Jan. 28, 2021

(86) PCT No.: PCT/US2021/015417
§ 371 (c)(1),
(2) Date: Jul. 29, 2022

(87) PCT Pub. No.: WO2021/154942
PCT Pub. Date: Aug. 5, 2021

(65) Prior Publication Data
US 2023/0341492 A1   Oct. 26, 2023

Related U.S. Application Data

(60) Provisional application No. 62/968,733, filed on Jan. 31, 2020.

(51) Int. Cl.
G01R 33/56    (2006.01)
G01R 33/563   (2006.01)
G06N 3/0464   (2023.01)

(52) U.S. Cl.
CPC ... G01R 33/5608 (2013.01); G01R 33/56358 (2013.01); G06N 3/0464 (2023.01)

(58) Field of Classification Search
None
See application file for complete search history.

(56) References Cited

U.S. PATENT DOCUMENTS 5,592,085 A      1/1997  Ehman
2019/0343488 A1* 11/2019 Dong ............... A61B 8/485

FOREIGN PATENT DOCUMENTS

WO   2019/099986 A1      5/2019
WO   WO-2019099986 A1 *  5/2019  ............ A61B 5/055

OTHER PUBLICATIONS

International Search Report of related PCT/US2021/015417, mailed on May 17, 2021, 4 pages.

(Continued)

*Primary Examiner* — Rodney E Fuller
(74) *Attorney, Agent, or Firm* — Quarles & Brady LLP

(57) ABSTRACT

In accordance with some embodiments, systems, methods, and media for estimating a mechanical property based on a transformation of magnetic resonance elastography (MRE) data using a trained artificial neural network are provided. In some embodiments, a system is provided, the system comprising: a hardware processor programmed to: receive displacement data of tissue in vivo; provide the displacement data to a trained ANN that was trained using noisy input datasets as training data, and derivative datasets corresponding to the noisy input datasets to evaluate performance during training, such that the trained ANN provides an output dataset corresponding to an analytical solution to a (Continued)

derivative of a function represented in an unlabeled input dataset thereby transforming the unlabeled input dataset into its derivative; receive, from the trained ANN, an output dataset indicative of a derivative of the displacement data; and estimate stiffness of the tissue based on the derivative.

21 Claims, 14 Drawing Sheets

(56) References Cited

OTHER PUBLICATIONS

Written Opinion of related PCT/US2021/015417, mailed on May 17, 2021, 7 pages.
Chatelin, Simon, et al: An automatic differentiation-based gradient method for inversion of the shear wave equation in magnetic resonance elastography: specific application in fibrous soft tissues1, Physics in Medicine and Biology, Institute of Physics Publishing, Bristol GB, vol. 61, No. 13, Jun. 14, 2016 (Jun. 14, 2016), pp. 5000-5019.
Kingma et al., "Adam: A Method for Stochstic Optimzation," ArXiv (2014): pp. 1-15, www.arxiv.org/abs/1412.6980.
Murphy, Matthew C., et al. "Artificial neural networks for stiffness estimation in magnetic resonance elastography." Agnetic Resonance in Medicine, 80.1 (2018): pp. 351-360.
Murphy et al., "Measuring the Characteristic Topography of Brain Stiffness with Magnetic Resonance Elastography," PLoS One (2013); pp. 1-14.
Szegedy et al., "Inception-v4, inception-resnet and the impact of residual connections on learning," Thirty-First AAAI Conference on Artificial Intelligence (2017): pp. 4278-4284.
Vemuri et al., "Alzheimer's Disease Diagnosis in Individual Subjects Using Structural MR Images: Validations Studies," Neuroimage (2008): pp. 1-25.
Ashburner, J., et al. (2005). Unified Segmentation. NeuroImage. 26. 839-51. 10.1016/j.neuroimage.2005.02.018.
Capizzi, Giacomo, et al. "A neural network approach for the differentiation of numerical solutions of 3-D electromagnetic problems." IEEE transactions on magnetics 40.2 (2004): 953-956.
Cardaliaguet, Pierre, and Guillaume Euvrard. "Approximation of a function and its derivative with a neural network." Neural networks 5.2 (1992): 207-220.
Hind, D., Sumner, M., & Gerada, C. (Sep. 2015). Estimating current derivatives for sensorless motor drive applications. In 2015 17th European Conference on Power Electronics and Applications (EPE'15 ECCE-Europe) (pp. 1-10). IEEE.

* cited by examiner

SYSTEMS, METHODS, AND MEDIA FOR ESTIMATING A MECHANICAL PROPERTY BASED ON A TRANSFORMATION OF MAGNETIC RESONANCE ELASTOGRAPHY DATA USING A TRAINED ARTIFICIAL NEURAL NETWORK

CROSS-REFERENCE TO RELATED APPLICATIONS

This application represents the national stage entry of PCT/US 2021/015417, filed on Jan. 28, 2021 and is based on, claims the benefit of, and claims priority to, U.S. Provisional Application No. 62/968,733, filed Jan. 31, 2020, the contents of which is hereby incorporated herein by reference in its entirety for all purposes.

STATEMENT REGARDING FEDERALLY SPONSORED RESEARCH

This invention was made with government support under EB001981 and EB027064 awarded by the National Institutes of Health. The government has certain rights in the invention.

BACKGROUND

Magnetic resonance elastography (MRE) is a magnetic resonance imaging (MRI)-based technique that is used to estimate stiffness of tissues within the body, and can be analogized to manual palpation, a technique that has a long history in the practice of medicine. However, while manual palpation has long been practiced for organs that are readily accessible from the exterior of a patient's body, MRE can be used to estimate stiffness of less accessible tissue, such as stiffness of brain tissue.

Conventional MRE generally includes introducing shear waves into a tissue-of-interest by mechanical vibration. Next, the resulting tissue displacement is imaged by a phase-contrast MRI pulse sequence with motion encoding gradients that are synchronized to the motion. Finally, these displacement images are mathematically inverted to calculate tissue stiffness.

MRE is growing in clinical impact, particularly for applications in the liver, where it is used to noninvasively assess fibrosis with high accuracy. Furthermore, brain stiffness has shown sensitivity to a number of physiological processes including neurodegenerative disease, normal aging, and even behavioral performance. Techniques used to compute stiffness from displacement images often use inversion algorithms that require the estimation of derivatives of the displacement data, which often has a relatively low signal-to-noise ratio (e.g., on the order of 1 to 100 when defined as a ratio of the range of amplitudes within the patch to the standard deviation of zero-mean Gaussian noise). The performance of conventional techniques for estimating the derivative of data having a relatively low signal to noise ratio, such as finite differences-based techniques, amplify noise and often produce biased estimates. While these deficiencies may be overcome by conventional regularized estimation, the appropriate regularization transform, function, and weighting term must be correctly identified for a given application, a non-trivial task.

Elastography can also be performed with other imaging modalities, such as ultrasound and some optical techniques. Many of these elastography techniques have similarities to MRE in the sense that shear waves are introduced into the tissue, or material being analyzed, and the resulting displacements are measured by the imaging modality. To this end, the inversion algorithms used to compute stiffness and other mechanical properties from displacement data generated using such imaging modalities also often rely on the calculation of derivatives, and as such share challenges with MRE.

Accordingly, systems, methods, and media for estimating a mechanical property based on a transformation of magnetic resonance elastography data using a trained artificial neural network are desirable.

SUMMARY

In accordance with some embodiments of the disclosed subject matter, systems, methods, and media for estimating a mechanical property based on a transformation of magnetic resonance elastography data using a trained artificial neural network are provided.

In accordance with some embodiments of the disclosed subject matter, a system for estimating a mechanical property based on a transformation of MRE data is provided, the system comprising: at least one hardware processor that is programmed to: receive displacement data from an MRE data source, wherein the displacement data represents displacements of tissue in vivo; provide the displacement data to a trained artificial neural network (ANN), wherein the trained ANN was trained using a plurality of noisy input datasets as training data, each of the plurality of noisy input datasets corresponding to a function of a plurality of functions, and using one or more derivative datasets corresponding to the noisy input datasets to evaluate performance of the ANN during training, such that the trained ANN provides one or more output datasets corresponding to an analytical solution to a derivative of a function represented in an unlabeled input dataset thereby transforming the unlabeled input dataset into one or more derivatives of the unlabeled input dataset; receive, from the trained ANN, an output dataset indicative of a derivative of the displacement data; and estimate stiffness of the tissue based on the derivative of the displacement data.

In some embodiments, the plurality of functions are wave-like functions.

In some embodiments, each of the plurality of functions includes no less than three independent variables.

In some embodiments, the at least one hardware processor is further programmed to: receive the plurality of functions; generate a plurality of input datasets using the plurality of functions, wherein each of the plurality of input datasets comprises a plurality of elements, each of the plurality of elements representing an output value of a particular function of the plurality of functions given a particular combination of input values; identify, for each of the plurality of functions, at least one derivative; generate, for each of the plurality of functions, a derivative dataset using the at least one derivative, wherein the derivative dataset comprises a plurality of elements, each of the plurality of elements representing a value of the derivative of the function given a particular combination of input values; generate, for each of the plurality of input datasets, at least one noisy input dataset by adding an error term to at least a subset of the plurality of elements, such that the plurality of noisy input datasets is generated with each noisy input dataset corresponding to one of the plurality of functions and one or more of the derivative datasets; and train an ANN using the plurality of noisy input datasets as training data, and using the one or more derivative datasets corresponding to the noisy input datasets to evaluate performance of the artificial neural network during training, such that the trained ANN is generated.

In some embodiments, the at least one hardware processor is further programmed to generate, for at least one of the plurality of input datasets, a first noisy input dataset by excluding at least a second subset of the plurality of elements such that the first noisy input dataset comprises fewer elements than the input dataset from which it was generated.

In some embodiments, the derivative of the displacement data comprises a first partial derivative of the displacement data with respect to a first independent variable, and the at least one hardware processor is further programmed to: receive, from the trained ANN, a second output dataset indicative of a second partial derivative of the displacement data with respect to a second independent variable; and estimate stiffness of the tissue based on the first partial derivative of the displacement data and the second partial derivative of the displacement data.

In some embodiments, the trained ANN comprises a convolutional neural network (CNN) that includes a plurality of filter modules, including a first filter module, a second filter module, and a third filter module, each having the same topology, wherein the first filter module is followed by a first batch normalization layer and a first rectified linear unit (ReLU) layer, an output of the first filter module is combined with an output of the second filter module via a residual connection followed by a second batch normalization layer and a second ReLU layer, and the output of the first filter module and the output of the second filter module is combined with an output of the third filter module via a second residual connection followed by a third batch normalization layer and a third ReLU layer, and wherein the ANN is configured to receive as input a 7×7×7×3 array of values representing a displacement field representing the displacement along each of three orthogonal coordinates across a 7×7×7 voxel block, and the ANN is configured to provide as an output three values, each of the values representing an estimate, at the central voxel of the 7×7×7 voxel block, of the partial derivative of the displacement field represented in the 7×7×7×3 along one of the three orthogonal coordinates.

In accordance with some embodiments of the disclosed subject matter, a method for estimating a mechanical property based on a transformation of MRE data is provided, comprising: receiving displacement data from an MRE data source, wherein the displacement data represents displacements of tissue in vivo; providing the displacement data to a trained artificial neural network (ANN), wherein the trained ANN was trained using a plurality of noisy input datasets as training data, and using one or more derivative datasets corresponding to the noisy input datasets to evaluate performance of the ANN during training, such that the trained ANN provides one or more output datasets corresponding to an analytical solution to a derivative of a function represented in an unlabeled input dataset thereby transforming the unlabeled input dataset into one or more derivatives of the unlabeled input dataset; receiving, from the trained ANN, an output dataset indicative of a derivative of the displacement data; and estimating stiffness of the tissue based on the derivative of the displacement data.

In some embodiments, a non-transitory computer readable medium containing computer executable instructions that, when executed by a processor, cause the processor to perform a method for estimating a mechanical property based on a transformation of magnetic resonance elastography (MRE) data is provided, the method comprising: receiving displacement data from an MRE data source, wherein the displacement data represents displacements of tissue in vivo; providing the displacement data to a trained artificial neural network (ANN), wherein the trained ANN was trained using a plurality of noisy input datasets as training data, and using one or more derivative datasets corresponding to the noisy input datasets to evaluate performance of the ANN during training, such that the trained ANN provides one or more output datasets corresponding to an analytical solution to a derivative of a function represented in an unlabeled input dataset thereby transforming the unlabeled input dataset into one or more derivatives of the unlabeled input dataset; receiving, from the trained ANN, an output dataset indicative of a derivative of the displacement data; and estimating stiffness of the tissue based on the derivative of the displacement data.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

DETAILED DESCRIPTION

In accordance with various embodiments, mechanisms (which can, for example, include systems, methods, and media) for estimating a mechanical property based on a transformation of magnetic resonance elastography data using a trained artificial neural network are provided.

In accordance with some embodiments of the disclosed subject matter, mechanisms described herein can utilize learning-based techniques to improve the accuracy of numerical differentiation compared to a finite difference approach. In some embodiments, appropriate regularization can be achieved by selection of a forward model used to generate training data. Though many potential applications exist for the mechanisms described herein, detailed examples are described in the context of magnetic resonance elastography, and specifically in connection with computing the curl of the displacement field, as such a computation is often performed before inversion to remove effects caused by longitudinal waves on the estimated mechanical properties.

Figure 1:
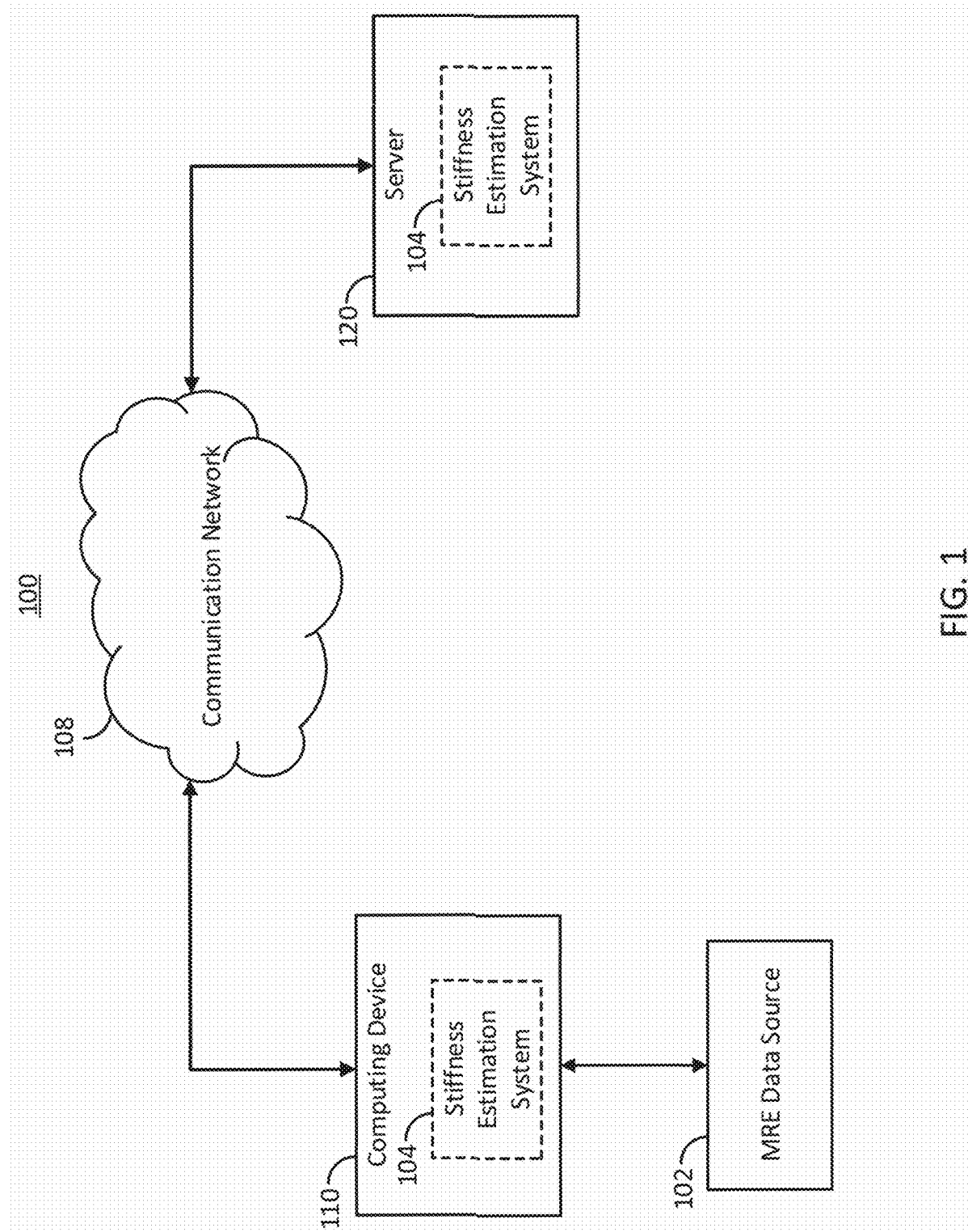
FIG. 1 shows an example of a system for estimating a mechanical property based on a transformation of magnetic resonance elastography data using a trained artificial neural network in accordance with some embodiments of the disclosed subject matter.

FIG. 1 shows an example 100 of a system for estimating a mechanical property based on a transformation of magnetic resonance elastography data using a trained artificial neural network (ANN) in accordance with some embodiments of the disclosed subject matter. As shown in FIG. 1, a computing device 110 can receive MRE data from MRE data source 102. In some embodiments, computing device 110 can execute at least a portion of a stiffness estimation system 104 to automatically estimate the stiffness of tissue represented in the MRE data.

Additionally or alternatively, in some embodiments, computing device 110 can communicate information about MRE data, such as displacement data, received from MRE data source 102 to a server 120 over a communication network 108, which can execute at least a portion of stiffness estimation system 104 to automatically estimate the stiffness of tissue represented by the MRE data. In such embodiments, server 120 can return information to computing device 110 (and/or any other suitable computing device) indicative of an output of stiffness estimation system 104.

In some embodiments, MRE data can include displacement data represented as wave images obtained using an MRE scan. For example, computing device 110 can provide displacement data by receiving the displacement data from MRE data source 102 and/or retrieving previously acquired displacement data from a memory or other suitable data storage. As another example, computing device 110 can acquire displacement data using an MRI system (e.g., MRE data source 102) that is in communication with computer device. In some embodiments, for example as described below in connection with FIG. 7, computing device 110 can form a part of an MRI system. In some embodiments, displacement data can be acquired by operating an MRI system to perform any suitable MRE scan, such as an MRE scan described in U.S. Pat. No. 5,592,085, which is hereby incorporated herein by reference in its entirety. Additionally or alternatively, in some embodiments, displacement data can be obtained using other imaging modalities and/or techniques. For example, elastography data can be obtained using ultrasound elastography techniques. As another example, elastography data can be obtained using optical elastography techniques.

In general, displacement data is representative of displacements occurring in a subject while displacement data is acquired. In some embodiments, the displacement data can be representative of time-harmonic displacement fields. Additionally or alternatively, in some embodiments, displacement data can be representative of transient displacement fields.

In some embodiments, displacement data can represent displacements caused by a single wave source, or by multiple wave sources. More generally, displacement data can represent displacements associated with a single wave field or with multiple wave fields. In some embodiments, displacement data can represent simultaneous, multifrequency displacement.

In some embodiments, computing device 110 and/or server 120 can be any suitable computing device or combination of devices, such as a desktop computer, a laptop computer, a smartphone, a tablet computer, a wearable computer, a server computer, a virtual machine being executed by a physical computing device, etc. As described below in connection with FIGS. 3-6 and 9-12, in some embodiments, stiffness estimation system 104 can: receive MRE data from MRE data source 102 (e.g., an MRI system); provide the MRE data to an ANN trained to provide one or more derivatives of the MRE data and/or one or more derivatives modified by the application of one or more operators; receive an estimate of the one or more derivatives of the MRE data from the trained ANN; and use the one or more derivatives to calculate the stiffness of tissue represented by the MRE data.

In some embodiments, MRE data source 102 can be any suitable source of MRE data, such as an MRI machine, another computing device (e.g., a server storing MRE data), etc. In some embodiments, MRE data source 102 can be local to computing device 110. For example, MRE data source 102 can be incorporated with computing device 110 (e.g., computing device 110 can be configured as part of a device for capturing and/or storing MRE data). As another example, MRE data source 102 can be connected to computing device 110 by a cable, a direct wireless link, etc. Additionally or alternatively, in some embodiments, MRE data source 102 can be located locally and/or remotely from computing device 110, and can communicate MRE data to computing device 110 (and/or server 120) via a communication network (e.g., communication network 108).

In some embodiments, communication network 108 can be any suitable communication network or combination of communication networks. For example, communication network 108 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, etc. In some embodiments, communication network 108 can be a local area network, a wide area network, a public network (e.g., the Internet), a private or semi-private network (e.g., a corporate or university intranet), any other suitable type of network, or any suitable combination of networks. Communications links shown in FIG. 1 can each be any suitable communications link or combination of communications links, such as wired links, fiber optic links, Wi-Fi links, Bluetooth links, cellular links, etc.

Figure 2:
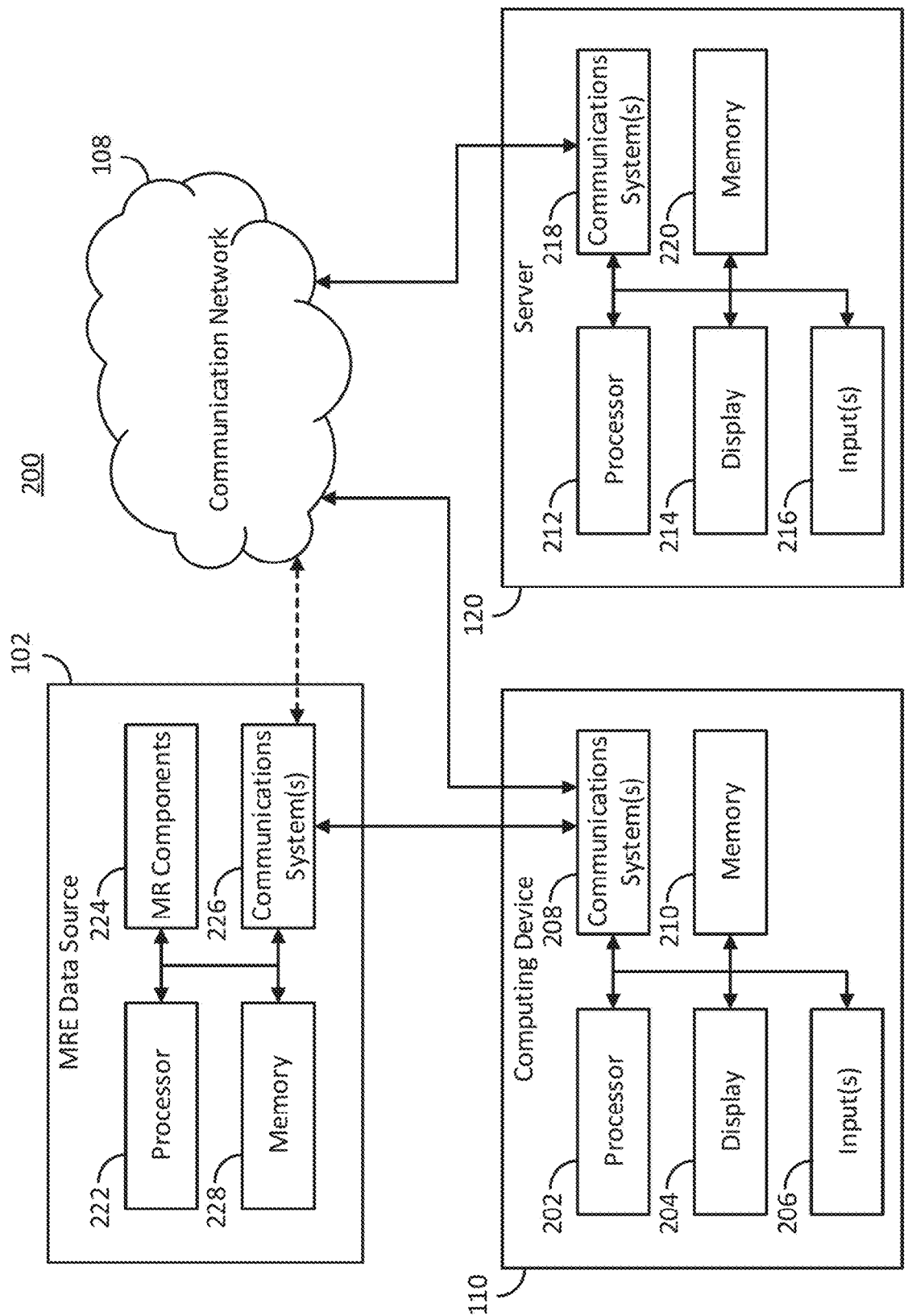
FIG. 2 shows an example of hardware that can be used to implement MRE data source, computing device, and/or server in accordance with some embodiments of the disclosed subject matter.

FIG. 2 shows an example 200 of hardware that can be used to implement MRE data source 102, computing device 110, and/or server 120 in accordance with some embodiments of the disclosed subject matter. As shown in FIG. 2, in some embodiments, computing device 110 can include a processor 202, a display 204, one or more inputs 206, one or more communication systems 208, and/or memory 210. In some embodiments, processor 202 can be any suitable hardware processor or combination of processors, such as a central processing unit (CPU), a graphics processing unit (GPU), etc. In some embodiments, display 204 can include any suitable display devices, such as a computer monitor, a touchscreen, a television, etc. In some embodiments, inputs 206 can include any suitable input devices and/or sensors that can be used to receive user input, such as a keyboard, a mouse, a touchscreen, a microphone, etc.

In some embodiments, communications systems 208 can include any suitable hardware, firmware, and/or software for communicating information over communication network 108 and/or any other suitable communication networks. For example, communications systems 208 can include one or more transceivers, one or more communication chips and/or chip sets, etc. In a more particular example, communications systems 208 can include hardware, firmware and/or software that can be used to establish a Wi-Fi connection, a Bluetooth connection, a cellular connection, an Ethernet connection, etc.

In some embodiments, memory 210 can include any suitable storage device or devices that can be used to store instructions, values, etc., that can be used, for example, by processor 202 to present content using display 204, to communicate with server 120 via communications system(s) 208, etc. Memory 210 can include any suitable volatile memory, non-volatile memory, storage, or any suitable combination thereof. For example, memory 210 can include RAM, ROM, EEPROM, one or more flash drives, one or more hard disks, one or more solid state drives, one or more optical drives, etc. In some embodiments, memory 210 can have encoded thereon a computer program for controlling operation of computing device 110. In such embodiments, processor 202 can execute at least a portion of the computer program to present content (e.g., MRI images, stiffness estimates, user interfaces, graphics, tables, etc.), receive content from server 120, transmit information to server 120, etc.

In some embodiments, server 120 can include a processor 212, a display 214, one or more inputs 216, one or more communications systems 218, and/or memory 220. In some embodiments, processor 212 can be any suitable hardware processor or combination of processors, such as a CPU, a GPU, etc. In some embodiments, display 214 can include any suitable display devices, such as a computer monitor, a touchscreen, a television, etc. In some embodiments, inputs 216 can include any suitable input devices and/or sensors that can be used to receive user input, such as a keyboard, a mouse, a touchscreen, a microphone, etc.

In some embodiments, communications systems 218 can include any suitable hardware, firmware, and/or software for communicating information over communication network 108 and/or any other suitable communication networks. For example, communications systems 218 can include one or more transceivers, one or more communication chips and/or chip sets, etc. In a more particular example, communications systems 218 can include hardware, firmware and/or software that can be used to establish a Wi-Fi connection, a Bluetooth connection, a cellular connection, an Ethernet connection, etc.

In some embodiments, memory 220 can include any suitable storage device or devices that can be used to store instructions, values, etc., that can be used, for example, by processor 212 to present content using display 214, to communicate with one or more computing devices 110, etc. Memory 220 can include any suitable volatile memory, non-volatile memory, storage, or any suitable combination thereof. For example, memory 220 can include RAM, ROM, EEPROM, one or more flash drives, one or more hard disks, one or more solid state drives, one or more optical drives, etc. In some embodiments, memory 220 can have encoded thereon a server program for controlling operation of server 120. In such embodiments, processor 212 can execute at least a portion of the server program to transmit information and/or content (e.g., MRI data, MRE data, results of a stiffness estimation, a user interface, etc.) to one or more computing devices 110, receive information and/or content from one or more computing devices 110, receive instructions from one or more devices (e.g., a personal computer, a laptop computer, a tablet computer, a smartphone, etc.), etc.

In some embodiments, MRE data source 102 can include a processor 222, magnetic resonance (MR) components 224, one or more communications systems 226, and/or memory 228. In some embodiments, processor 222 can be any suitable hardware processor or combination of processors, such as a CPU, a GPU, etc. In some embodiments, MR components 224 can be any suitable components to generate MRE data. An example of an MRI machine that can be used to implement MRE data source 102 is described below in connection with the MRI system of FIG. 7. Other examples of MRI machines that can be used to implement MRE data source 102 can include conventional MRI scanners (e.g., a 1.5 T scanner, a 3 T scanner), high field MRI scanners (e.g., a 7 T scanner), open bore MRI scanners, etc. In some embodiments, MRE data source 102 can be implemented using an MRI machine that is specially configured to perform head and/or brain scans. For example, MRE data source 102 can be implemented using a compact 3 T scanner that generates asymmetrical gradients, and that is adapted for performing head and/or brain scans.

Note that, although not shown, MRE data source 102 can include any suitable inputs and/or outputs. For example, MRE data source 102 can include input devices and/or sensors that can be used to receive user input, such as a keyboard, a mouse, a touchscreen, a microphone, a trackpad, a trackball, hardware buttons, software buttons, etc. As another example, MRE data source 102 can include any suitable display devices, such as a computer monitor, a touchscreen, a television, etc., one or more speakers, etc.

In some embodiments, communications systems 226 can include any suitable hardware, firmware, and/or software for communicating information to computing device 110 (and, in some embodiments, over communication network 108 and/or any other suitable communication networks). For example, communications systems 226 can include one or more transceivers, one or more communication chips and/or chip sets, etc. In a more particular example, communications systems 226 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, etc.

In some embodiments, memory 228 can include any suitable storage device or devices that can be used to store instructions, values, MM data, MRE data, etc., that can be used, for example, by processor 222 to: control MR components 224, and/or receive MR data from MR components 224; generate MR data; present content (e.g., MR images, stiffness data, a user interface, etc.) using a display; communicate with one or more computing devices 110; etc. Memory 228 can include any suitable volatile memory, non-volatile memory, storage, or any suitable combination thereof. For example, memory 228 can include RAM, ROM, EEPROM, one or more flash drives, one or more hard disks, one or more solid state drives, one or more optical drives, etc. In some embodiments, memory 228 can have encoded thereon a program for controlling operation of MR data source 102. In such embodiments, processor 222 can execute at least a portion of the program to generate MRE data, transmit information and/or content (e.g., MRE data) to one or more computing devices 110, receive information and/or content from one or more computing devices 110, receive instructions from one or more devices (e.g., a personal computer, a laptop computer, a tablet computer, a smartphone, etc.), etc.

Figure 3:
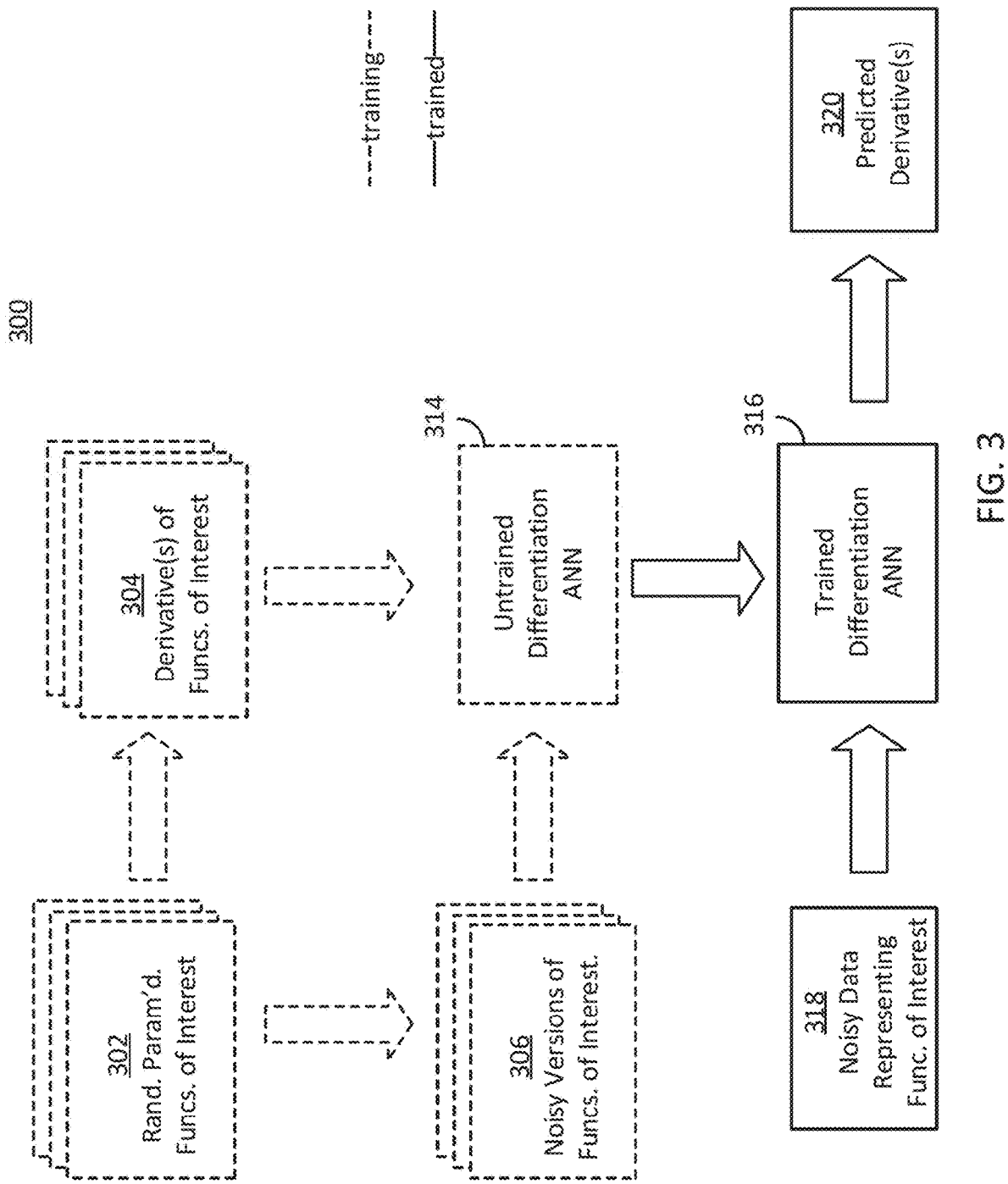
FIG. 3 shows an example of a flow for training and using mechanisms for estimating a derivative of a function represented in data that has a relatively low signal-to-noise ratio using a trained artificial neural network in accordance with some embodiments of the disclosed subject matter.

FIG. 3 shows an example 300 of a flow for training and using mechanisms for estimating a derivative of a function represented in data that has a relatively low signal-to-noise ratio using a trained ANN in accordance with some embodiments of the disclosed subject matter. As shown in FIG. 3, a set 302 of randomly parameterized functions that are similar to a function of interest can be used to generate training data. In some embodiments, any suitable functions can be chosen to use as training data, and any suitable number and variety of functions can be generated to use as training data. For example, wave-like functions can be selected for use as training data for estimating derivatives of MRE data due to the wave-like nature of MRE data caused by the shear waves introduced into the tissue. In a more particular example, training data can be derived using a function that describes a wave traveling through a homogeneous viscoelastic material, such as $u(r) = r^{-1} e^{-\alpha r} \sin(kr - \varphi_0)$, where u represents the displacement of the material from its initial state, r is the distance from the wave source, $\alpha$ is an attenuation coefficient, k is the wave number, and $\varphi_0$ is the initial phase.

In some embodiments, randomly parameterized functions 302 can be randomly parameterized within any suitable range of parameters. For example, the value of one or more coefficients can be randomly selected to fall within a predetermined range, and the value of one or more constants can be randomly selected to fall within a predetermined range. In such an example, the predetermined range can be a range that approximates the range of expected values from the phenomenon of interest, such as displacement data in MRE data. In a more particular example, the function that describes the wave traveling through a homogenous viscoelastic material can be used to generate randomly parameterized functions 302 by randomly assigning a wave number from a range that is expected to reflect the spatial frequencies for a given application (e.g., in a range of 0.5 kilopascals (kPa) to 5 kPa for normal brain tissue), as well as the speed of sound in water (e.g., about 1500 m/s) to approximate the effects of longitudinal waves. In some embodiments, functions 302 can be regularly parameterized, and/or the parameters can be selected to correspond to parameters that commonly occur in the observed data that is being modeled. In such embodiments, randomization can be introduced when noise is introduced and/or when data is intentionally omitted during creation of noisy datasets.

In some embodiments, one or more derivatives 304 can be analytically determined for each function in the set of randomly parameterized functions 302. For example, for each function, a partial derivative of the function can be analytically identified with respect to each of one or more variables. As another example, a total derivative of the function can be analytically determined with respect to all of the variables. In some embodiments, after identifying derivatives 304, each derivative can be discretized to create a dataset representing the derivative 304 of a particular randomly parameterized function 302 over a particular range (e.g., in any suitable coordinate system, such as in a volume defined in Cartesian coordinates).

In some embodiments, one or more noisy datasets 306 representing discretized versions of the randomly parameterized functions 302 can be generated by converting the function into a dataset that has a relatively low signal-to-noise ratio by introducing errors in the data and/or by omitting data points at one or more locations within the data set. For example, for a function having three variables (e.g., three spatial variables x, y, and z), the function can be converted to a three dimensional array of values representing the output of the function at discrete combinations of input values. In such an example, at various elements in the array, an error term (e.g., symbolized by $\in$) can be added to the value where the error term can take a random value in a range that is determined based on a desired signal to noise ratio (e.g., based on an estimated signal to noise ratio in observed data, such as a signal to noise ratio estimated from MRE data), and/or the value can be omitted to simulate data that was not properly recorded.

In a particular example, noisy datasets 306 can be generated by converting a randomly parameterized function 302 or group of randomly parameterized functions 302 that were generated from the function that describes the wave traveling through a homogenous viscoelastic material into a dataset of values by randomly placing up to five wave sources at random locations outside of a volume representing a particular noisy dataset 306, with each wave source being represented as a random combination of k, α, and $\varphi_0$. The displacement caused by each source can be calculated for locations in the volume representing the particular noisy dataset 306, and the combined displacement caused by the combination of sources can be used to set initial values for the particular noisy dataset 306. Similarly, the combined derivative of the displacement caused by the combination of sources can be determined (e.g., by adding the individual contribution of each derivative) for use during training. In such an example, noisy datasets 306 can be generated for a 7×7×7 grid with 3-mm isotropic spacing between voxels to match the spacing in data acquired using MRE techniques with the wave sources placed outside the grid. As described above, an error term ∈ noise can then be added to one or more of the values in the dataset, and/or values can be masked and/or removed from the dataset (e.g., from the 7×7×7 grid) to generate the noisy datasets 306. In a particular example, Zero-mean Gaussian noise can be added to one or more values in the noisy dataset 306 with a randomly selected signal-to-noise ratio in the range of 1 to 50. Additionally, in some embodiments, to improve curl estimates at edges, a randomly selected mask patch taken from in vivo MRE data can be applied to one or more of the noisy datasets 306 (e.g., as described below in connection with 406 of FIG. 4). In some embodiments, the values within noisy datasets 306 can be normalized to fall within a particular range. For example, each noisy dataset can be normalized to have values that fall in a range of [−1,1]. In such an example, the target outputs (e.g., corresponding derivatives 304) can also be normalized to be on the same scale as the inputs. However, this is merely an example, and the noisy datasets can be normalized within any suitable range (or not normalized).

In some embodiments, noisy datasets 306 can be used as training data during a training procedure for an untrained differentiation ANN 314, and one or more derivatives 304 corresponding to the analytical solution to the function represented by a particular noisy dataset can be used as a label during training identifying the correct output classification for the particular input dataset. In some embodiments, differentiation ANN 314 can have any suitable topology and/or hyperparameters, and can be trained using any suitable technique or combination of techniques. In some embodiments, noisy datasets 306 and corresponding derivatives 304 (or combinations of derivatives) can be used to train a convolutional neural network that has a network topology that has some similarities to Inception-based networks (e.g., as described in Szegedy et al., "Inception-v4, inception-resnet and the impact of residual connections on learning," Thirty-First AAAI Conference on Artificial Intelligence (2017), which is hereby incorporated by reference herein in its entirety. An example of such network topology is described below in connection with FIGS. 5A and 5B. Such a network architecture can be implemented and trained, for example, using the Keras API with a TensorFlow backend, to estimate the three partial spatial derivatives at the central voxel of the patch given the noisy, masked simulated displacements.

In some embodiments, a trained differentiation ANN 316 resulting from the training procedure can be used to predict the analytical solution for an unlabeled noisy dataset representing a function that is expected to be similar to the functions selected for inclusion in the set of randomly parameterized functions 302. For example, a noisy data set 318 that is expected to represent a wave-like function can be provided as input to trained differentiation ANN 316, and trained differentiation ANN 316 can provide one or more predicted derivatives 320 of noisy dataset 318. In such an example, if noisy dataset 318 is MRE data, predicted derivatives 320 can be used in the estimation of stiffness values of the tissue represented in the MRE data.

Figure 4:
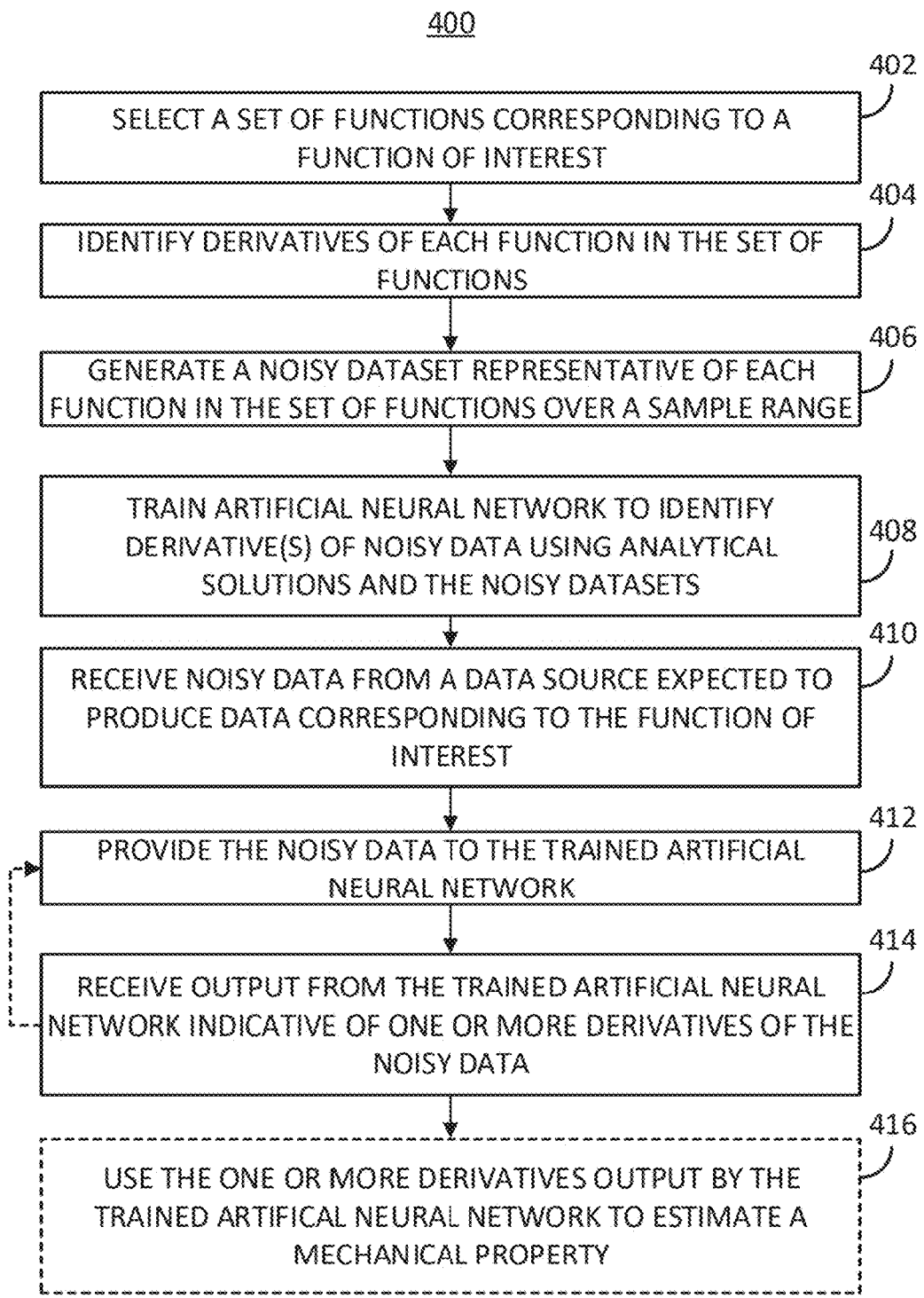
FIG. 4 shows an example of a process for estimating a mechanical property based on a transformation of magnetic resonance elastography data using a trained artificial neural network in accordance with some embodiments of the disclosed subject matter.

FIG. 4 shows an example 400 of a process for estimating a mechanical property based on a transformation of magnetic resonance elastography data using a trained artificial neural network in accordance with some embodiments of the disclosed subject matter. In some embodiments, at 402, process 400 can include selecting a set of function corresponding to a function of interest for inclusion in training data. For example, process 400 can include selecting a set of functions that are similar to a function that can be used to model data representing a phenomenon of interest, where the derivative of the function is useful for estimating one or more properties related to the phenomenon. In a more particular example, wave-like functions that have similar properties to wave-like functions that can be used to model displacements in tissue in MRE data can be selected for inclusion in the set of training data.

In some embodiments, the set of functions selected at 402 can be diversified by randomly parameterizing the functions. For example, multiple versions of each function can be generated with one or more coefficients and/or constants randomized to diversify the set of functions. In such an example, the coefficient(s) and/or constant(s) can be randomized within a range that is similar to a range that is expected to be observed in the functions that can be used to model the data representing the phenomenon of interest.

At 404, process 400 can include identifying one or more derivatives of each of the functions in the set of functions selected at 402. In some embodiments, any suitable technique or set of techniques can be used to identify the derivative(s) of each function in the set of functions. Note that although the mechanisms described herein are generally described using partial derivatives as examples of targets for training, this is merely an example, and other quantities based on the derivative, such as the gradient, curl, and/or divergence can be used as a target for training in addition to, or in lieu of, the derivative or partial derivatives of the function. For example, rather than merely finding the derivative of a function, a composite differential quantity, such as gradient, curl, and/or divergence can be found and used during training. In such an example, the output of the trained ANN can be the curl, in addition to, or in lieu of, a derivative. However, in some applications, such an approach may be impractical. For example, in the case of MRE, the coordinate system of the data may not be known, and may need to be derived (e.g., by testing a number of combinations, such as sign flips and permutations of the partial derivatives of the data to find the combination that minimizes the divergence, which should be small in the case of incompressible tissue).

In some embodiments, process 400 can also include discretizing the derivative(s) identified at 404 over a sample range for input to the ANN during a training procedure. For example, for a derivative of a function having three variables (e.g., three spatial variables x, y, and z), the derivative can be converted to a three dimensional array of values representing the value of the derivative at discrete combinations of input values that fall within the sample range.

At 406, process 400 can generate a noisy dataset representative of each function in the set of functions selected at 402 over a sample range (e.g., a sample range that is co-extensive with the sample range at which the derivative was discretized). In some embodiments, any suitable technique or combination of techniques can be used to generate the noise dataset. For example, process 400 can convert each function into a dataset that has a relatively low signal-to-noise ratio by generating an array of values representing the output of the function at discrete combinations of input values across the sample range. As described above in connection with noisy datasets 306 of FIG. 3, in some embodiments, the function or functions used to generate the noisy datasets can be sampled at a resolution that matches the expected resolution of the data of interest. Alternatively, in some embodiments, the functions or functions can be trained in units of voxels$^{-1}$, and the output can be converted to distance. In such an example, process 400 can add an error term $\in$ (which can have a negative value or a positive value) to one or more of the positions in the array. In addition to, or in lieu of, adding error term E, process 400 can exclude data points from the array to create missing data. Any suitable technique or combination of techniques can be used to exclude data from the array. For example, brain masks and a lobar atlas can be computed and transformed into MRE space to facilitate generation of training data. In such an example, brain masks can be computed by segmentation of T1-weighted images to produce probabilistic maps of gray matter, white matter, and cerebral spinal fluid using SPM5-techniques with a custom template and priors (e.g., as described in Ashburner et al., "Unified Segmentation," Neurimage (2015), and Vemuri et al., "Alzheimer's Disease Diagnosis in Individual Subjects Using Structural MR Images: Validations Studies," Neuroimage (2008), each of which are hereby incorporated by reference herein in its entirety). Tissue probability maps along with a lobar atlas can then be registered and resampled to the MRE magnitude image using the T1-weighted image as the reference image (e.g., as described in Murphy et al., "Measuring the Characteristic Topography of Brain Stiffness with Magnetic Resonance Elastography," PLoS One (2013), which is here hereby incorporated by reference herein in its entirety). Voxels for which the probabilities of gray matter plus white matter were greater than cerebrospinal fluid (CSF) can be included in the brain mask, and voxels for which the probabilities of gray matter plus white matter were less than CSF can be excluded from the brain mask. The masks can also segmented into 5 subregions, which can be chosen to avoid inversion of data across major dural folds (e.g., that act as wave sources) and the lateral sulcus (where CSF separates anatomically distinct regions and expands due to atrophy). These subregions can include the cerebellum; the union of the frontal lobes; deep gray matter and white matter; parietal lobe and corpus callosum (left and right hemispheres); and the union of the occipital and temporal lobes (left and right hemispheres). For each training example, a mask patch can be randomly selected from an example a brain mask generated from in vivo MR data, and can be applied to the noisy dataset, and voxels in the noisy dataset corresponding to CSF in the mask can be excluded from the noisy dataset to simulate a region of the brain in which holes in MRE data collected in vivo are likely to exist. Note that although the mask patches described herein are randomly selected from a brain mask generated from in vivo MR data, this is merely an example, and mask patches can be selected from a simulated mask that is procedurally generated (e.g., using a set of rules), and/or procedurally generated directly (i.e., not selected from a larger mask).

In a more particular example, process 400 can convert functions having three variables (e.g., three spatial variables x, y, and z) to three dimensional arrays of values representing the output of the functions at discrete combinations of input values over the sample range, exclude data points from the arrays, and add a randomized error term to the remaining values in each array.

At 408, process 400 can train an ANN to identify derivatives of functions represented in noisy datasets using the noisy datasets generated at 406 as training data and the analytical solutions identified at 404 as labeled data used for calculating a loss function during training. In some embodiments, any suitable technique or combination of techniques can be used to train the ANN. For example, an ANN with an Inception-like topology (e.g., as described below in connection with FIGS. 5A and 5B) can be train to minimize mean absolute error (MAE) using an Adam optimizer (e.g., as described in Kingma et al., "Adam: A Method for Stochstic Optimzation," ArXiv (2014), available at arxiv(dot)org/abs/1412.6980, which is hereby incorporated by reference herein in its entirety) with a mini-batch size of 100 examples and 1000 mini-batches per epoch. Mini-batches of training data were generated in real time until the stopping criterion was reached. In some embodiments, training can be performed using any suitable learning rate (e.g., 0.001, 0.0003, 0.0001, etc.), and any suitable stopping condition can be used to determine when training is to be stopped (e.g., when the MAE has not improved for 3 consecutive epochs).

At 410, process 400 can receive noisy data (e.g., data having a relatively low signal-to-noise ratio) from a data source that is expected to produce data that can be modeled using functions having parameters similar to the parameters of the functions selected for inclusion in the set of functions at 402. For example, if the set of function selected at 402 were selected to be similar to displacement data produced during an MRE procedure, the data received by process 400 at 410 can be displacement data produced during an MRE procedure.

At 412, process 400 can provide the noisy data to the trained ANN in any suitable format. For example, process 400 can format the data received at 410 to have a similar format to the data used during training at 408.

At 414, process 400 can receive an output from the trained ANN that is indicative of one or more derivatives of the noisy data received at 410. For example, the trained ANN can provide an output in the form of the value of the derivative or the values of multiple derivatives at the central voxel of the input data. As another the trained ANN can provide an output in the form of an array having the same dimensions as the input, in which the values in the array are predicted values of the derivative of the function represented in the noisy dataset. In some embodiments, where the data input at 412 was only a portion of the noisy data received at 410 (e.g., a 7×7×7 block of the MRE data), process 400 can return to 412 to provide a next block of data to the trained ANN. Additional or alternatively, in some embodiments, multiple instances of the trained ANN can be executed in parallel, and process 400 can provide multiple blocks of data to the trained ANN instances in parallel. In some embodiments, outputs received at 414 can be combined into an array to generate derivative values for the entire set of noisy data received at 410.

At 416, process 400 can use the output of the trained ANN received at 414 to estimate a characteristic of interest. For example, where the noisy data received at 410 is EMR displacement data, at 416, process 400 can use the output of the trained ANN received at 414 to estimate stiffness of tissue represented in the EMR displacement data. As another example, where the noisy data received at 410 is stock price data, at 416, process 400 can use the output of the trained ANN received at 414 to estimate an option price for an equity.

In some embodiments, process 400 can be executed in parts and/or by multiple devices. For example, in a training phase, a first portion of process 400 can be executed by a first computing device (e.g., a computing device such as computing device 110 and/or a server such as, such as server 120) for training an ANN, and one or more other portions of process 400 can be executed by one or more other computing devices (e.g., computing device 110, server 120, and/or an MRI system such as the MRI system described below in connection with FIG. 7) for utilizing the trained ANN.

Figure 5A:
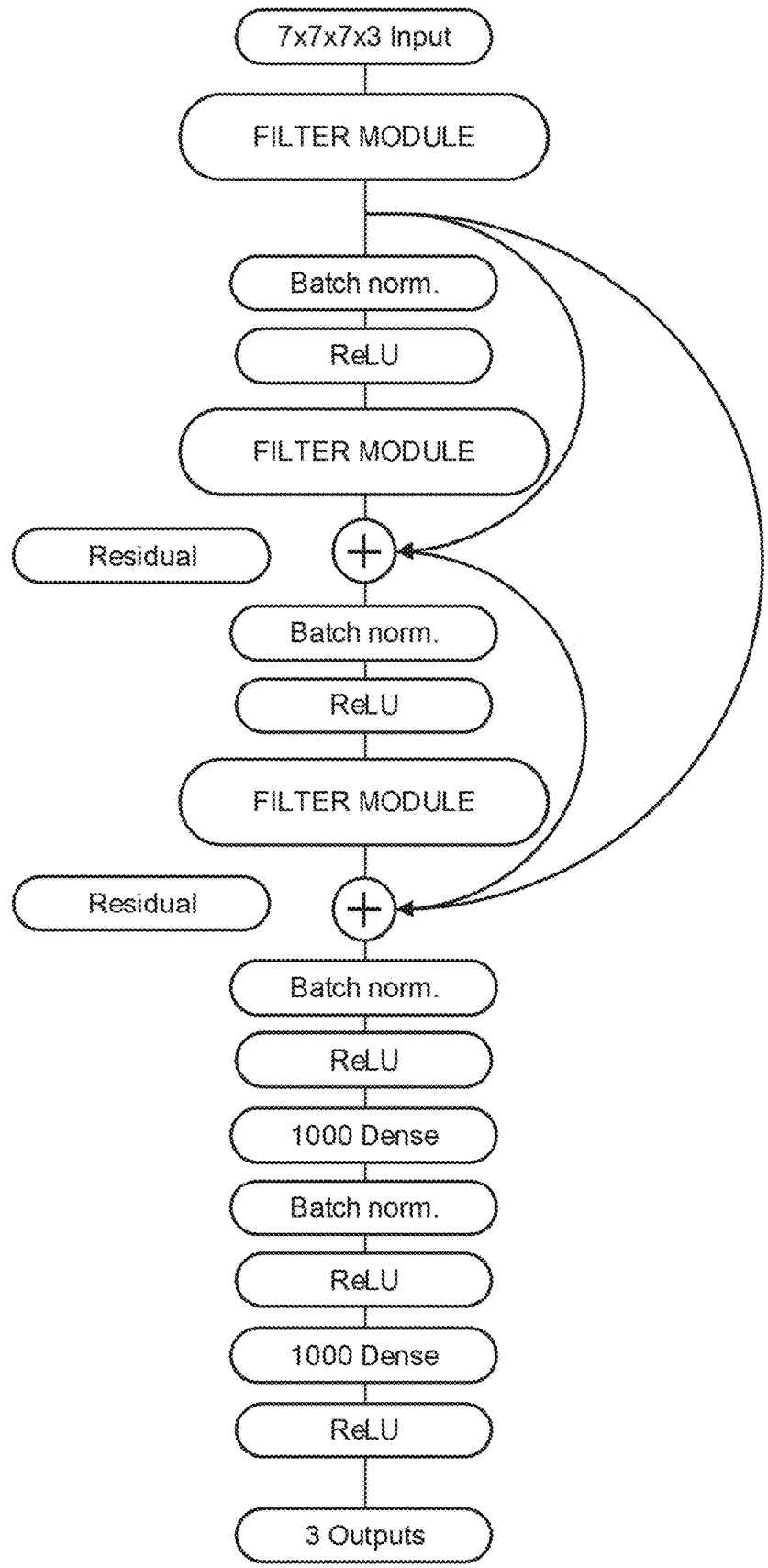
FIG. 5A shows an example of a topology of a convolutional neural network that can be trained to estimate a derivative of a function represented in data that has a relatively low signal-to-noise ratio in accordance with some embodiments of the disclosed subject matter.
Figure 5B:
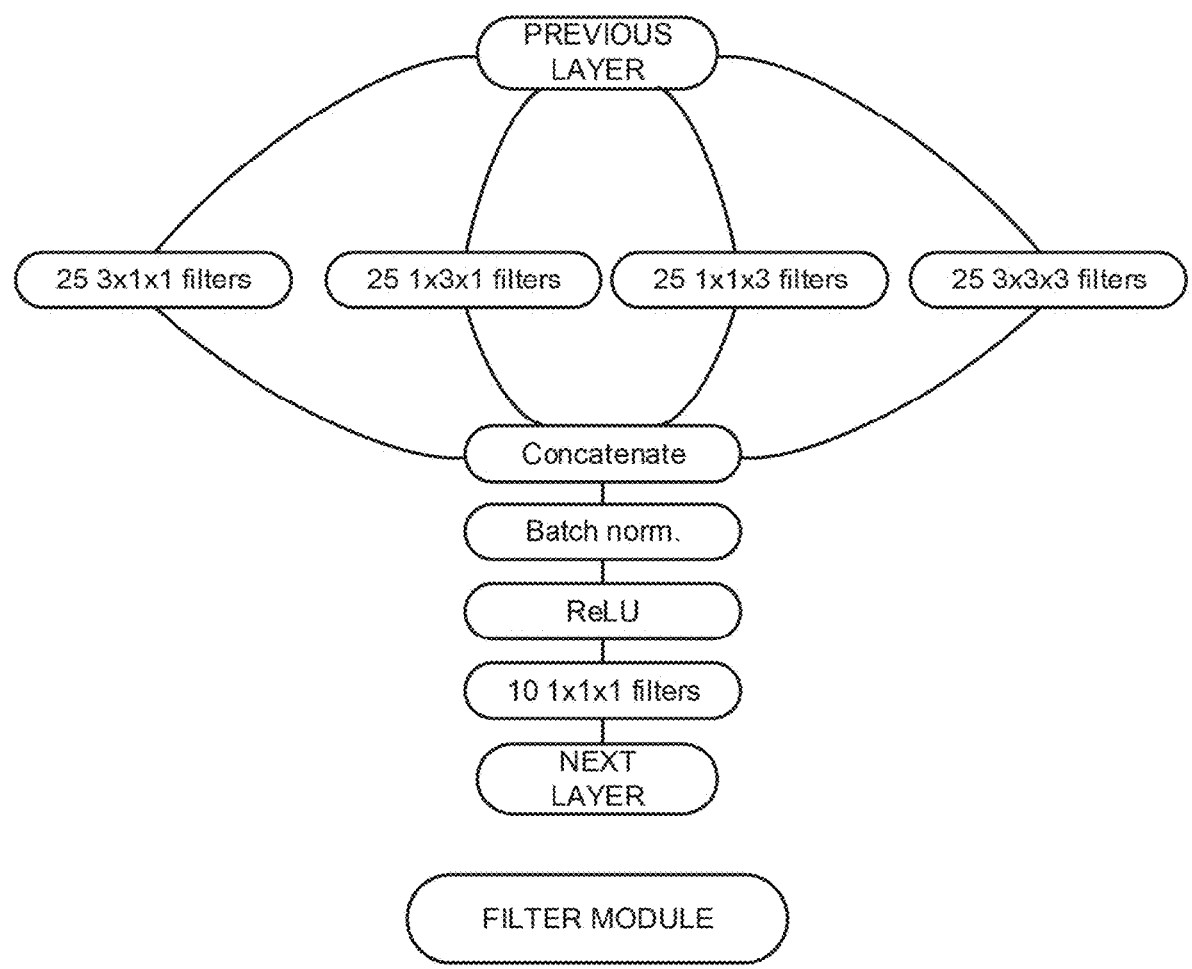
FIG. 5B shows an example of a filter module that can be used in the topology of FIG. 5A in accordance with some embodiments of the disclosed subject matter.

FIGS. 5A and 5B show examples of a topology of a convolutional neural network that can be trained to estimate a derivative of a function represented in data that has a relatively low signal-to-noise ratio, and a filter module that can be used in the topology of FIG. 5A, in accordance with some embodiments of the disclosed subject matter. As shown in FIG. 5A, the network can receive as input a dataset representing a 7×7×7 voxel block of data, with each voxel being associated with a three element vector representing the displacement in three orthogonal coordinates (e.g., x, y, and z) of the tissue at that vector. Alternatively, the data can be provided as three separate 7×7×7 blocks of data to 3 channels, with each block representing displacements along a different coordinate. The network can include filter modules that are schematically illustrated in FIG. 5B, and can combine the outputs of the filter modules using residual connections (e.g., as described in Szegedy et al., "Inception-v4, inception-resnet and the impact of residual connections on learning,"). In some embodiments, the output of the network topology shown in FIG. 5A can be trained to provide an estimate of the partial derivative at the central voxel of the 7×7×7 block along each coordinate. Accordingly, to determine the partial derivatives across an entire MRE dataset, the dataset can be provided to the network in 7×7×7 voxel blocks with a stride of 1, and the estimates can be combined to generate partial derivative estimates across the entire MRE dataset.

Figure 6:
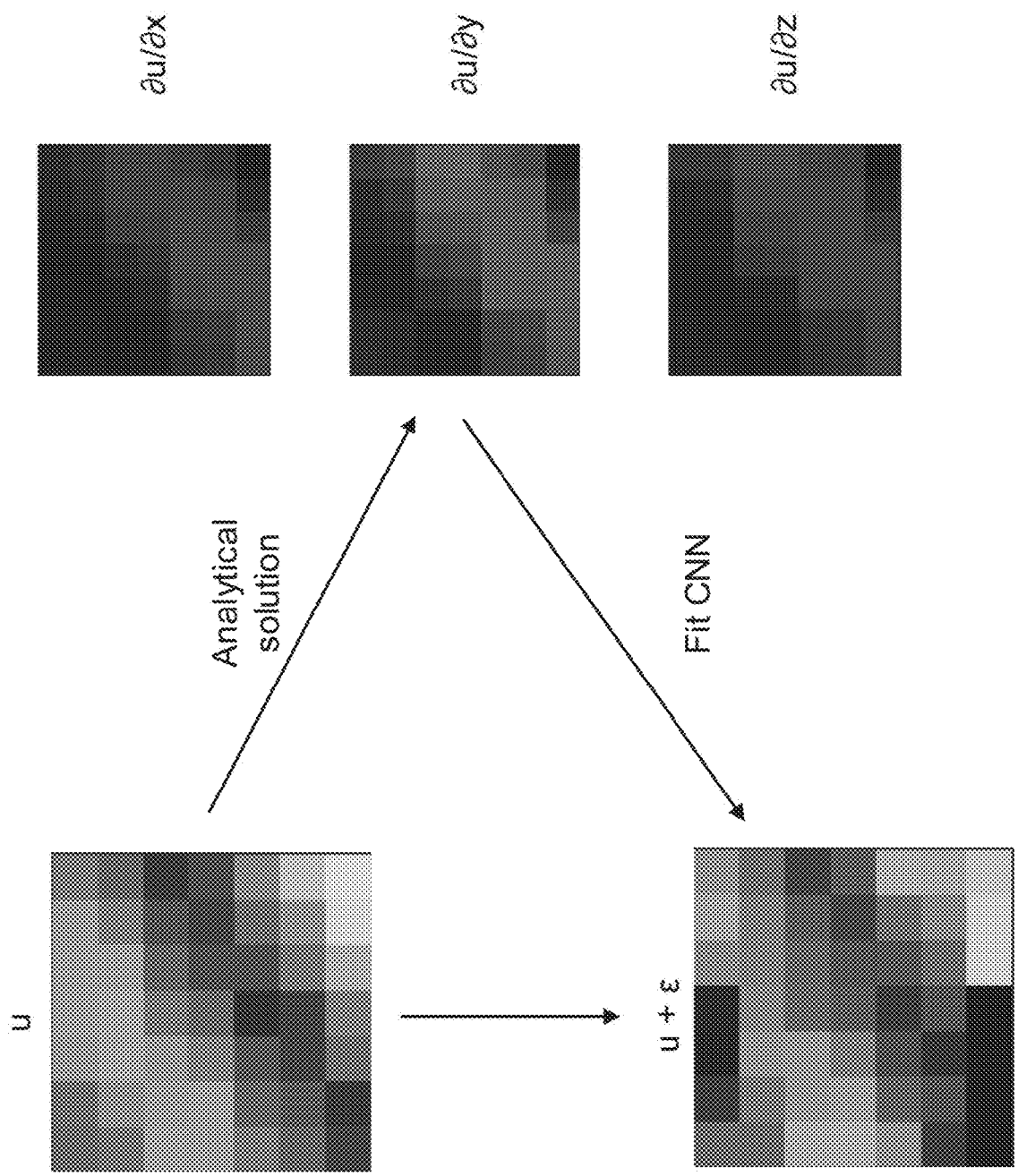
FIG. 6 shows an example of a dataset representing a noise-free version of a function representing a displacement field, analytical solutions to partial derivatives of the function, a dataset representing a low signal-to-noise version of the function, and how the various datasets are used during training of an artificial neural network in accordance with some embodiments of the disclosed subject matter.

FIG. 6 shows an example of a dataset representing a noise-free version of a function representing a displacement field, analytical solutions to partial derivatives of the function, a dataset representing a low signal-to-noise version of the function, and how the various datasets are used during training of an artificial neural network in accordance with some embodiments of the disclosed subject matter. In the upper left of FIG. 6, a discretized version of a portion of a function represented as a two-dimensional array of values (that is a single layer of a three dimensional array of values representing a three dimensional function) over a sample space is shown in which color maps to the magnitude of the value associated with each point in the array. The analytical solution for the partial derivatives of the function with respect to each variable (e.g., x, y, and z) can be determined, and a discretized version of the derivative can be generated for use during training. On the right hand side of FIG. 6, discretized versions of the partial derivatives with respect to x, y, and z are shown over the same sample space for which the values of the function in the upper left are shown.

As described above in connection with FIGS. 3 and 4, noise can be added to the function and one or more data points can be exclude from the array of values representing the discretized version of the function to generate a relatively low signal-to-noise ratio dataset (shown in the lower left of FIG. 6) representing the same function that is represented by the noise-free dataset shown in the upper left of FIG. 6. Note that because the derivatives were analytically determined from the function itself, and the noisy dataset was generated from the noise-free dataset representing the function, the derivatives are known to be the derivatives of the noisy dataset, which would be difficult to determine numerically (e.g., using finite differences techniques). Accordingly, the noisy dataset can be used as input to an ANN during a training phase, and the known derivative(s) of the noisy dataset can be used to evaluate the performance of the ANN during the training phrase such that the parameters and/or hyperparameters of the ANN can be tuned during training.

Figure 7:
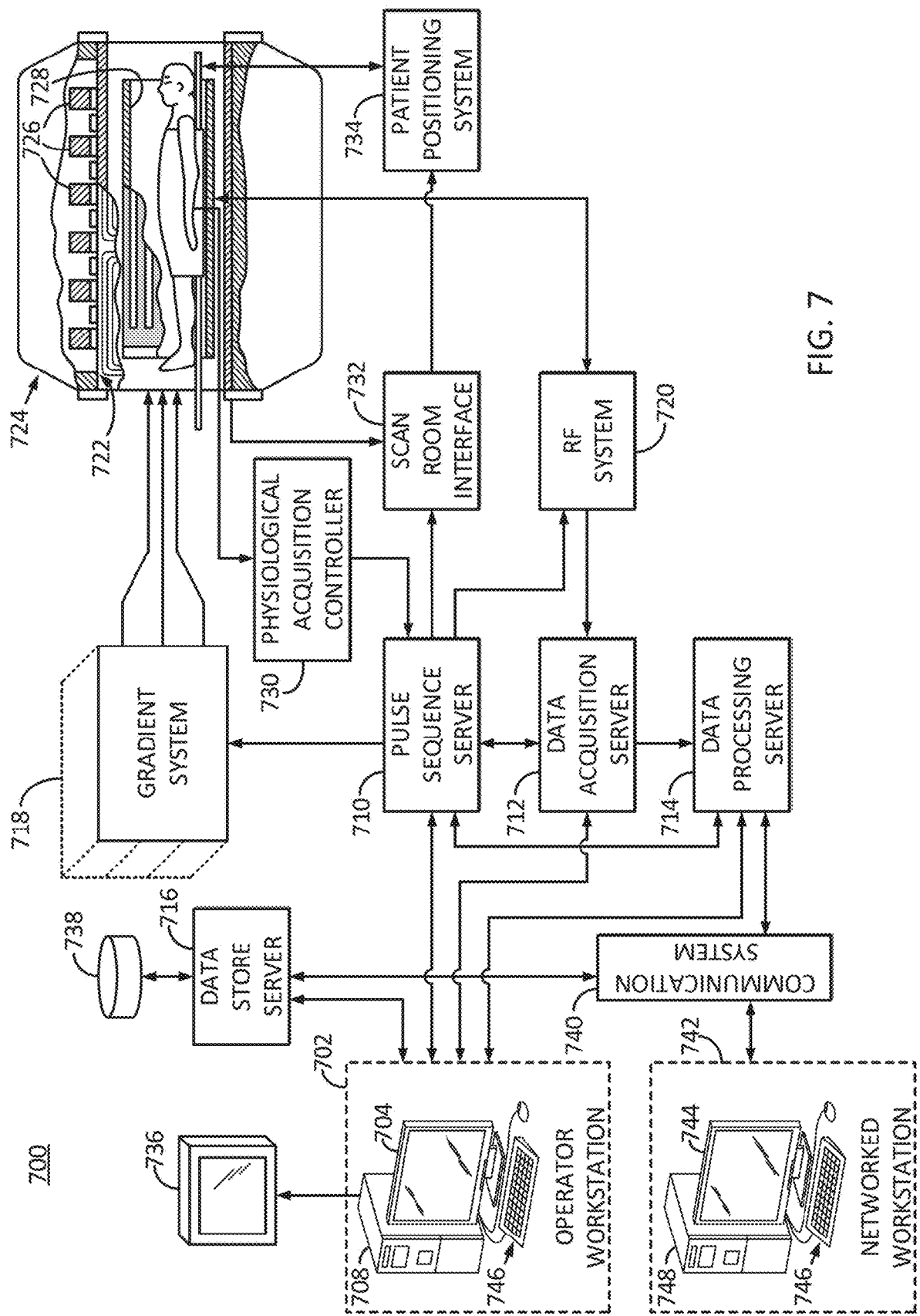
FIG. 7 shows an example of an MRI system that can be used to implement mechanisms described herein for estimating a mechanical property based on a transformation of magnetic resonance elastography data using a trained artificial neural network in accordance with some embodiments of the disclosed subject matter.

FIG. 7 shows an example 700 of an MRI system that can be used to implement mechanisms described herein for estimating a mechanical property based on a transformation of magnetic resonance elastography data using a trained artificial neural network in accordance with some embodiments of the disclosed subject matter. In some embodiments, MRI system 700 can include an operator workstation 702, which can include a display 704, one or more input devices 706 (e.g., a keyboard, a mouse), and a processor 708. In some embodiments, processor 708 can be implemented using a commercially available programmable machine executing a commercially available operating system. In some embodiments, operator workstation 702 can provide an operator interface to facilitate entering scan parameters into MM system 700. Additionally, in some embodiments, operator workstation 702 can be coupled to one or more servers, such as, for example, a pulse sequence server 710, a data acquisition server 712, a data processing server 714, and/or a data store server 716. In some embodiments, operator workstation 702 and servers 710, 712, 714, and/or 716 can be connected via a communication system 740, which can include wired and/or wireless network connections In some embodiments, pulse sequence server 710 functions in response to instructions provided by operator workstation 702 to operate a gradient system 718 and a radiofrequency (RF) system 720. Gradient waveforms for performing a prescribed scan can be produced and applied to the gradient system 718, which then excites gradient coils in an assembly 722 to produce the magnetic field gradients $G_x$, $G_y$, and $G_z$ that are used for spatially encoding magnetic resonance signals. In some embodiments, gradient coil assembly 722 forms part of a magnet assembly 724 that includes a polarizing magnet 726 and a whole-body RF coil 728.

In some embodiments, RF waveforms can be applied by RF system 720 to RF coil 728, or a separate local coil to perform the prescribed magnetic resonance pulse sequence. Responsive magnetic resonance signals detected by the RF coil 728, or a separate local coil, are received by RF system 720. The responsive magnetic resonance signals may be amplified, demodulated, filtered, and digitized under direction of commands produced by pulse sequence server 710. In some embodiments, RF system 720 can include an RF transmitter for producing a wide variety of RF pulses used in MRI pulse sequences. The RF transmitter can be responsive to the prescribed scan and direction from pulse sequence server 710 to produce RF pulses of the desired frequency, phase, and/or pulse amplitude waveform. The generated RF pulses can be applied to whole-body RF coil 728, to one or more local coils, and/or coil arrays.

In some embodiments, RF system 720 can also include one or more RF receiver channels. An RF receiver channel can include an RF preamplifier that amplifies a magnetic resonance signal received by coil 728 to which it is connected, and a detector that detects and digitizes I and Q quadrature components of the received magnetic resonance signal. The magnitude of the received magnetic resonance signal can, therefore, be determined at a sampled point by the square root of the sum of the squares of the I and Q components based on the following relationship:

$$M=\sqrt{I^2+Q^2},\quad (1)$$

and the phase of the received magnetic resonance signal can also be determined based on the following relationship:

$$\varphi = \tan^{-1}\left(\frac{Q}{I}\right). \quad (2)$$

In some embodiments, pulse sequence server 710 can receive patient data from a physiological acquisition controller 730. For example, physiological acquisition controller 730 can receive signals from one or more sensors connected to the patient, such as electrocardiograph (ECG) signals from electrodes, respiratory signals from a respiratory bellows or other respiratory monitoring devices, or other suitable signals generated by other types of sensors. In such an example, such signals can be used by the pulse sequence server 710 to synchronize, or "gate," the performance of the scan with the subject's heartbeat and/or respiration.

In some embodiments, pulse sequence server 710 can connect to a scan room interface circuit 732 that receives signals from various sensors associated with the condition of the patient and/or the magnet system. For example, through scan room interface circuit 732, a patient positioning system 734 can receive commands to move the patient to desired positions during the scan.

In some embodiments, digitized magnetic resonance signal samples produced by RF system 720 can be received by data acquisition server 712. In such embodiments, data acquisition server 712 can operate in response to instructions received (e.g., downloaded) from operator workstation 702 to receive the real-time magnetic resonance data and provide buffer storage, so that data is not lost by data overrun. In some embodiments, data acquisition server 712 can pass the acquired magnetic resonance data to data processor server 714. For example, for a scan that requires information derived from acquired magnetic resonance data to control the further performance of the scan, data acquisition server 712 can be programmed to produce such information and convey it to pulse sequence server 710. In a more particular example, during pre-scans, magnetic resonance data can be acquired and used to calibrate the pulse sequence performed by pulse sequence server 710. As another more particular example, navigator signals can be acquired and used to adjust the operating parameters of RF system 720 and/or gradient system 718, and/or to control the view order in which k-space is sampled. As yet another more particular example, data acquisition server 712 can process magnetic resonance signals used to detect the arrival of a contrast agent in a magnetic resonance angiography (MRA) scan. As another example, data acquisition server 712 can acquire magnetic resonance data and processes it in real-time to produce information that is used to control the scan.

In some embodiments, data processing server 714 can receive magnetic resonance data from data acquisition server 712 and processes the magnetic resonance data in accordance with instructions provided by operator workstation 702. For example, such processing can include reconstructing two-dimensional and/or three-dimensional images by performing a Fourier transformation of raw k-space data and/or other image reconstruction algorithms (e.g., iterative and/or backprojection reconstruction algorithms). As another example, such processing can include applying filters to raw k-space data and/or to reconstructed images. As yet another example, such processing can include generating functional magnetic resonance images. As sill another example, such processing can include calculating motion and/or flow images.

In some embodiments, images reconstructed by data processing server 714 can be conveyed back to operator workstation 702 for storage. Real-time images can be stored in a data base memory cache, from which they can be output to operator display 702 and/or a display 736. In some embodiments, batch mode images and/or selected real-time images can be stored in a host database using disc storage 738. When such images have been reconstructed and transferred to storage, data processing server 714 can notify data store server 716 on operator workstation 702. In some embodiments, operator workstation 702 can be used by an operator to, among other things, archive the images, produce films, and send the images via a network to other facilities.

In some embodiments, MRI system 700 can include one or more networked workstations 742. For example, a networked workstation 742 cam include a display 744, one or more input devices 746 (e.g., a keyboard, a mouse), and a processor 748. Networked workstation 742 can be located within the same facility as operator workstation 702, or in a different facility, such as a different healthcare institution or clinic.

In some embodiments, networked workstation 742 can gain remote access to data processing server 714 and/or data store server 716 via communication system 740. Additionally, although only a single networked workstation 742 is shown in FIG. 7, multiple networked workstations 742 can have access to data processing server 714 and data store server 716. Accordingly, magnetic resonance data, magnetic resonance elastography data, reconstructed images, and/or other data can be exchanged between data processing server 714, data store server 716, and one or more networked workstations 742, such that the data and/or images can be remotely processed by one or more authorized networked workstations 742.

Figure 8A:
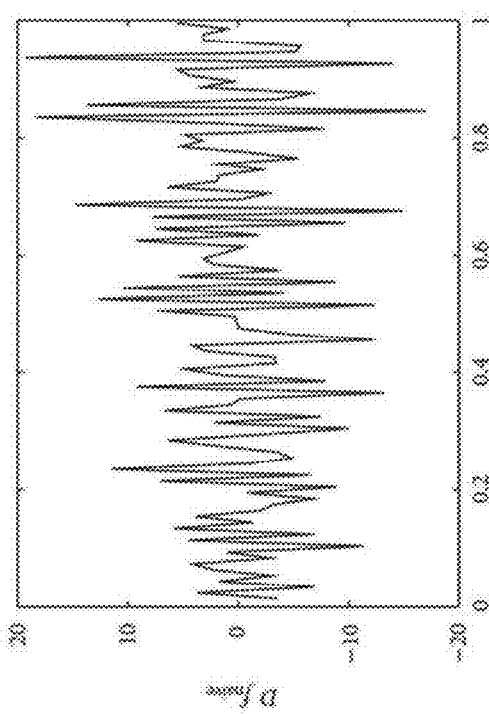
FIG. 8A shows an example of a low signal-to-noise dataset representing a function.

FIGS. 8A to 8D show examples of a low signal-to-noise dataset representing a function, a naïve estimate of the derivative of the underlying function, an estimate of the derivative of the underlying function after a denoise operation has been applied to the dataset, and the derivative of the underlying function determined by an analytical solution. In FIG. 8A, a dataset representing function that varies across 1 dimension (x) is shown for a sample range x=[0,1]. Because the function in the sample space is relatively simple (e.g., one function that can be used to model the dataset is a piecewise function in which $$f(x) = \begin{cases} 0.5 - x, & x < 0.5 \\ -0.5 + x, & x \geq 0.5 \end{cases},$$

many humans can deduce that such a function fits reasonably well as a denoised model of the dataset, and can relatively easily determine the pointwise derivative (shown in FIG. 8D) of the dataset based on the model. Note that because the dataset is limited to the sample space, other functions that behave differently outside of the sample space may also exhibit the same behavior within the sample space.

Figure 8B:
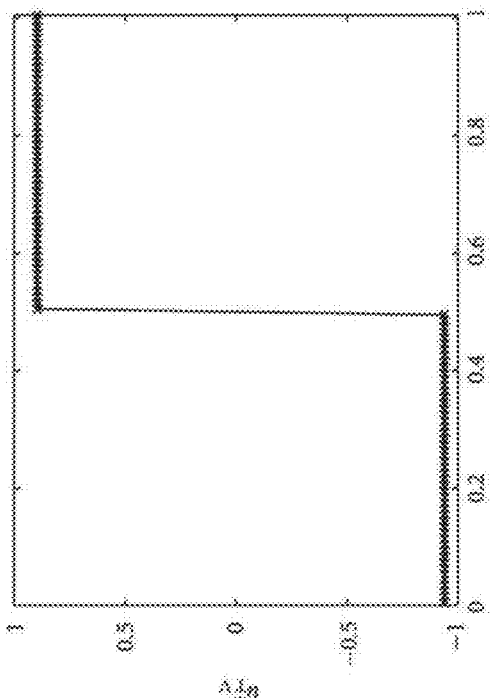
FIG. 8B shows an example of a naïve estimate of the derivative of the underlying function represented by the dataset.
Figure 8C:
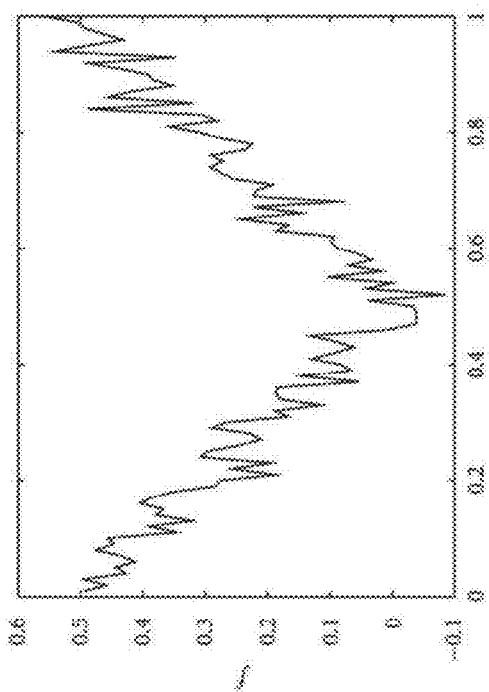
FIG. 8C shows an example of an estimate of the derivative of the underlying function after a denoise operation has been applied to the dataset.
Figure 8D:
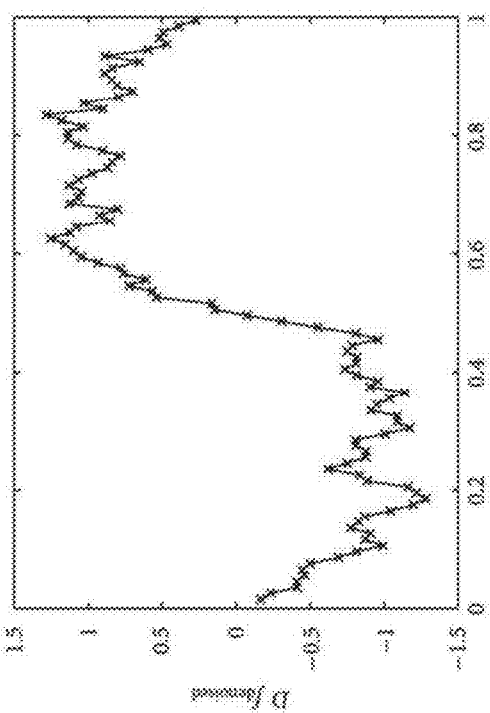
FIG. 8D shows an analytical solution to the derivative of the underlying function represented by the low signal-to-noise dataset of FIG. 8A.

However, as shown in FIGS. 8B and 8C, respectively, even when a relatively simple function can be used to model the dataset, both a naïve numerical technique and a more sophisticated technique that first applies a denoising algorithm both provide inaccurate estimates of the derivative. Of course, most datasets that represent interesting phenomena cannot be modeled by such simple functions, and in the case of MRE and other applications often involved datasets over three dimensions which humans have a much more difficult time analyzing than the simple dataset shown FIG. 8A. In some embodiments, mechanisms described herein can train an ANN using low signal-to-noise datasets (e.g., the dataset shown in FIG. 8A) and corresponding examples of the analytical solution of the derivative of the underlying function (e.g., the pointwise derivative shown in FIG. 8D), such as the derivative of a function that can be used to model the dataset within the sample space without noise, with high confidence. In such embodiments, a similar input dataset input to the trained ANN would be expected to produce an output that resembles FIG. 8D, rather than the noisy derivatives shown in FIGS. 8B and 8C, even though the exact pattern of noise in the dataset would be expected to be different.

Figure 9:
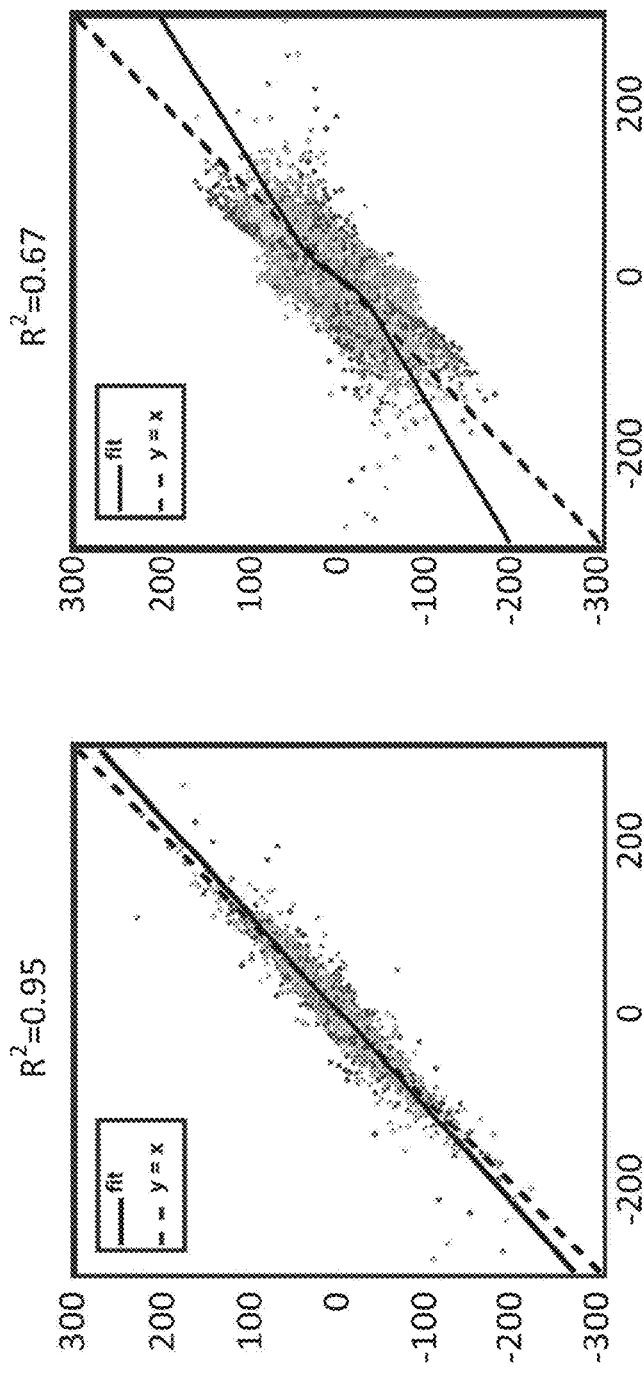
FIG. 9 shows an accuracy comparison between a derivative estimated from low signal-to-noise ratio data of a function using mechanisms described herein for estimating a derivative using a trained artificial neural network and a derivative estimated from low signal-to-noise ratio data of a function using finite differences with 3×3×3 smoothing and a 27 voxel kernel.

FIG. 9 shows an accuracy comparison between a derivative estimated from low signal-to-noise ratio data of a function using mechanisms described herein for estimating a derivative using a trained artificial neural network and a derivative estimated from low signal-to-noise ratio data of a function using finite differences with 3×3×3 smoothing and a 27 voxel kernel. The results shown in FIG. 9 were based on an ANN with a topology described above in connection with FIGS. 5A and 5B trained using data that was generated using analytical functions and then corrupted by noise and missing data to mimic measured displacement fields. The function described above in connection with FIG. 3 that describes a wave traveling through a homogeneous viscoelastic material (i.e., $u(r)=r^{-1}e^{-\alpha r}\sin(kr-\varphi_0)$, where u represents the displacement of the material from its initial state, r is the distance from the wave source, $\alpha$ is an attenuation coefficient, k is the wave number, and $\varphi_0$ is the initial phase) was used to generate the training data. To generate each training example, the equation and the analytical solutions to its partial derivatives were evaluated on a 7×7×7 grid with 3-mm isotropic spacing to match the acquired MRE data. Up to 5 wave sources were placed at random locations outside the patch with randomly assigned $\varphi_0$, as well as parameters k and a, which were chosen randomly from a range commonly observed in vivo. Zero-mean Gaussian noise was added to each example with a randomly selected signal-to-noise ratio in the range of 1 to 50. To improve curl estimates at edges, a randomly selected patch taken from an in vivo mask was applied to designate certain voxels for exclusion (e.g., to simulate the presence of CSF in the patch). Each example was scaled from −1 to 1. The ANN was then trained using the Keras API with a TensorFlow backend to estimate the three partial spatial derivatives at the central voxel of the patch given the noisy, masked simulated displacements. The network was fit to minimize mean absolute error (MAE) using an Adam optimizer with a mini-batch size of 100 examples and 1000 mini-batches per epoch. Mini-batches of training data were generated in real time until the stopping criterion was reached. Network fitting was performed at 3 learning rates (0.001, 0.0003, and 0.0001), each time stopping when the MAE was not improved for 3 consecutive epochs.

Each point in the scatter plots of FIG. 9 represents a partial derivative of a simulated data patch from the wave function described above (i.e., three points are plotted per example) calculated using mechanisms described herein, or using finite differences-based techniques. The color of the point represents the number of non-zero voxels in the randomly selected mask patch used to impose missing data (i.e., a lower number corresponds to more missing data). Note that the data generated by the wave function has derivatives that fall along the x-y line, and thus data points that are father from the line have a greater error.

Figure 10:
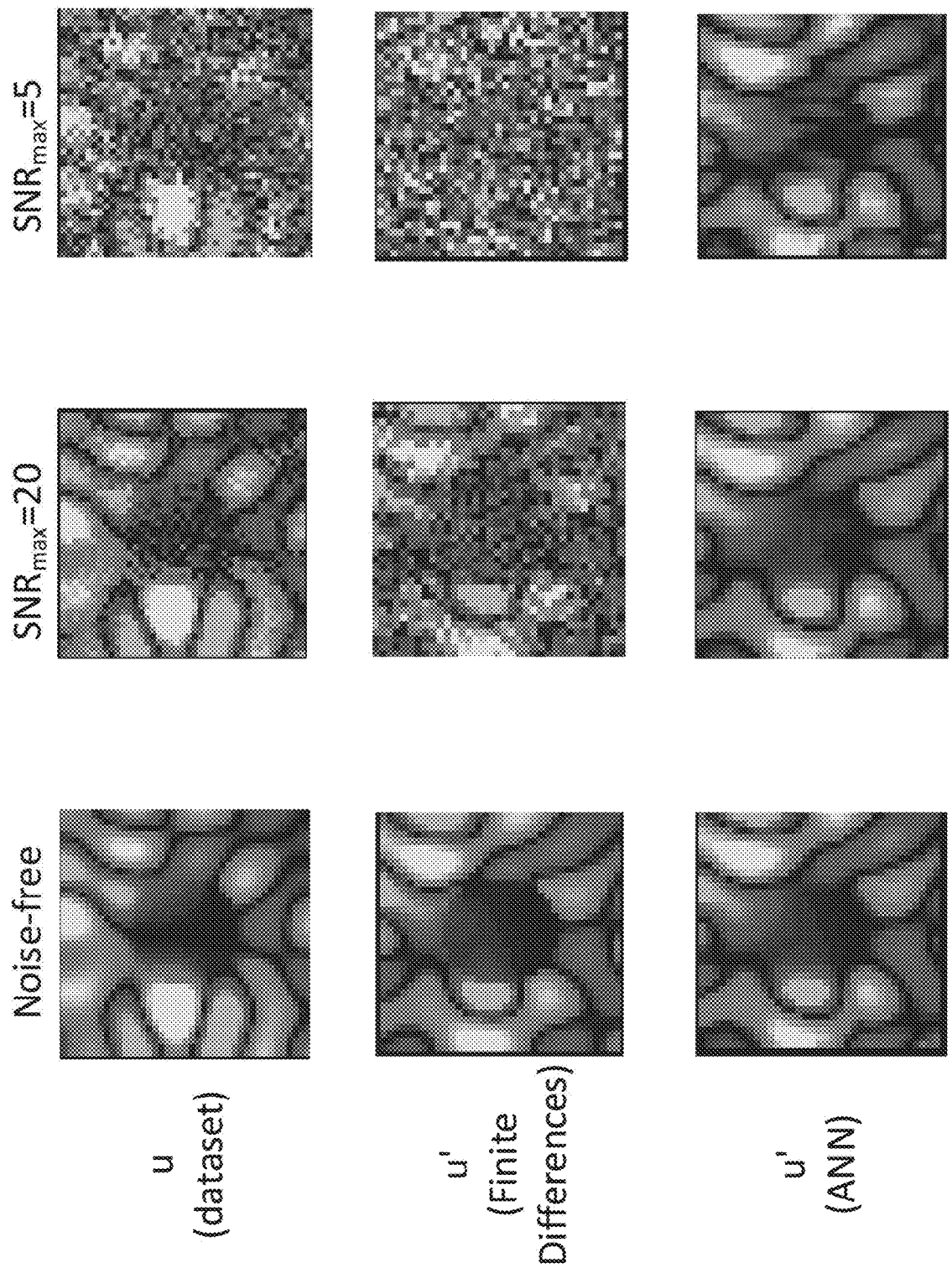
FIG. 10 shows an example showing datasets in the top row, derivatives estimated using finite differences techniques in the middle row, and derivatives estimated using mechanisms described herein for estimating a derivative using a trained artificial neural network in accordance with some embodiments of the disclosed subject matter.

FIG. 10 shows an example showing datasets in the top row, derivatives estimated using finite differences techniques in the middle row, and derivatives estimated using mechanisms described herein for estimating a derivative using a trained ANN in accordance with some embodiments of the disclosed subject matter. As shown in FIG. 10, on a noise-free dataset, finite differences techniques and mechanisms described herein for estimating a derivative of a function represented in data using a trained ANN produce comparable results. However, as the signal-to-noise ratio in the dataset decreases, the pointwise derivative estimates produced by the finite-differences techniques become noisy in proportion to the data, while the estimates produced using the trained ANN are much more stable and robust to noise in the underlying dataset.

Figure 11:
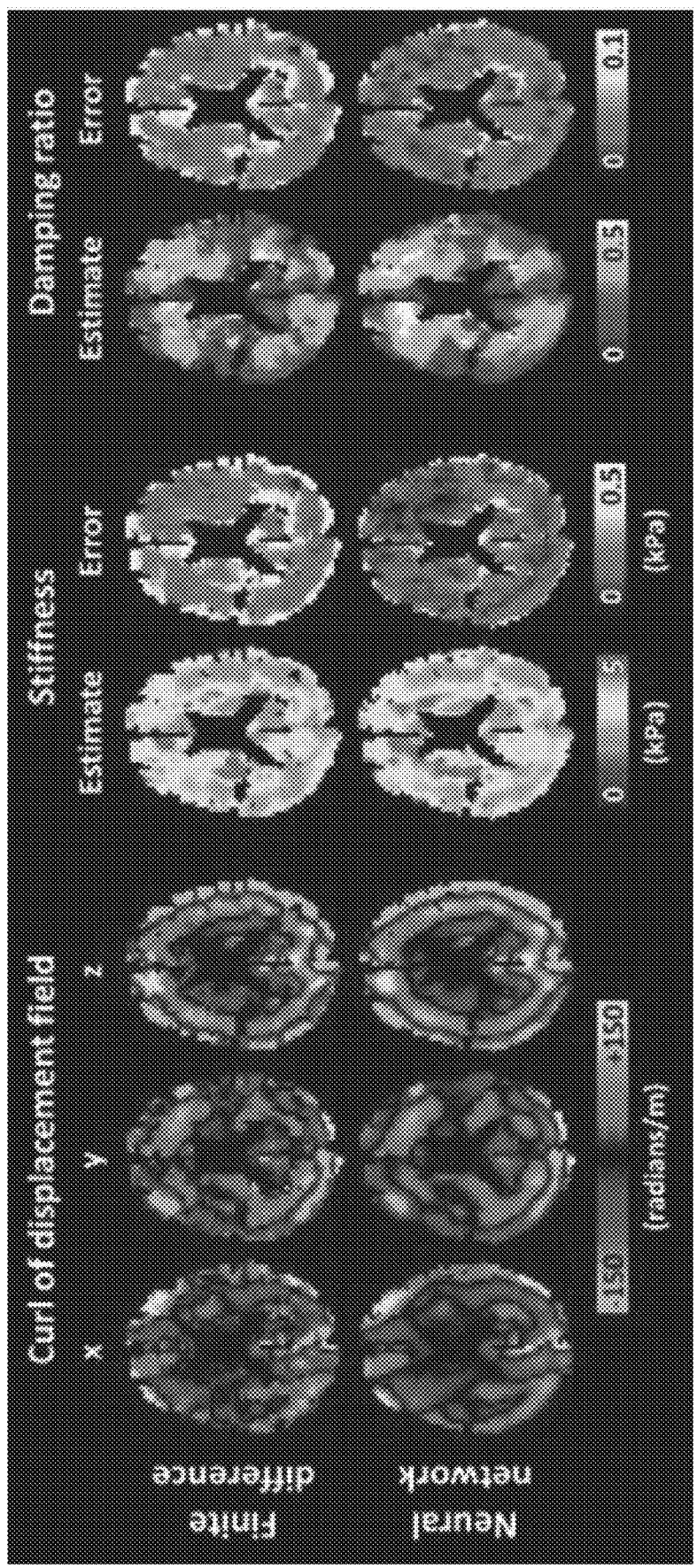
FIG. 11 shows MRE results generated using conventional techniques in the top row, and generated using mechanisms implemented in accordance with some embodiments of the disclosed subject matter for estimating a mechanical property based on a transformation of magnetic resonance elastography data using a trained artificial neural network.

FIG. 11 shows MRE results generated using conventional techniques in the top row, and generated using mechanisms implemented in accordance with some embodiments of the disclosed subject matter for estimating a mechanical property based on a transformation of magnetic resonance elastography data using a trained artificial neural network. In FIG. 11, curl values in units of radians/meter (radians/m) are depicted at various points in a single planar slice of a human brain from which MRE data has been collected. The curl values represent the value of the curl operator at each point calculated based on the partial derivative of the displacement field "u" (generated using MRE techniques) with respect to each axis (e.g., x, y, and z).

Also shown in FIG. 11 are stiffness estimates based on the x, y, and z curls, and corresponding error of the estimated stiffness values. In the top row are the three components of the curl of a displacement field measured using MRE that were computed using finite differences, along with the subsequent estimates of stiffness and damping ratio. Each of the mechanical property maps is accompanied by an error map, which was computed as the difference between the 75th and 25th percentiles of the prediction interval using quantile regression. Analogous results using the trained network described in connection with FIG. 9 to compute the curl are shown in the bottom row. Note that the stiffness estimate and damping ratio derived from derivative estimates produced by the trained ANN appears visually smoother and less noisy, which is confirmed by the error data, which shows fewer areas with high error values.

Figure 12:
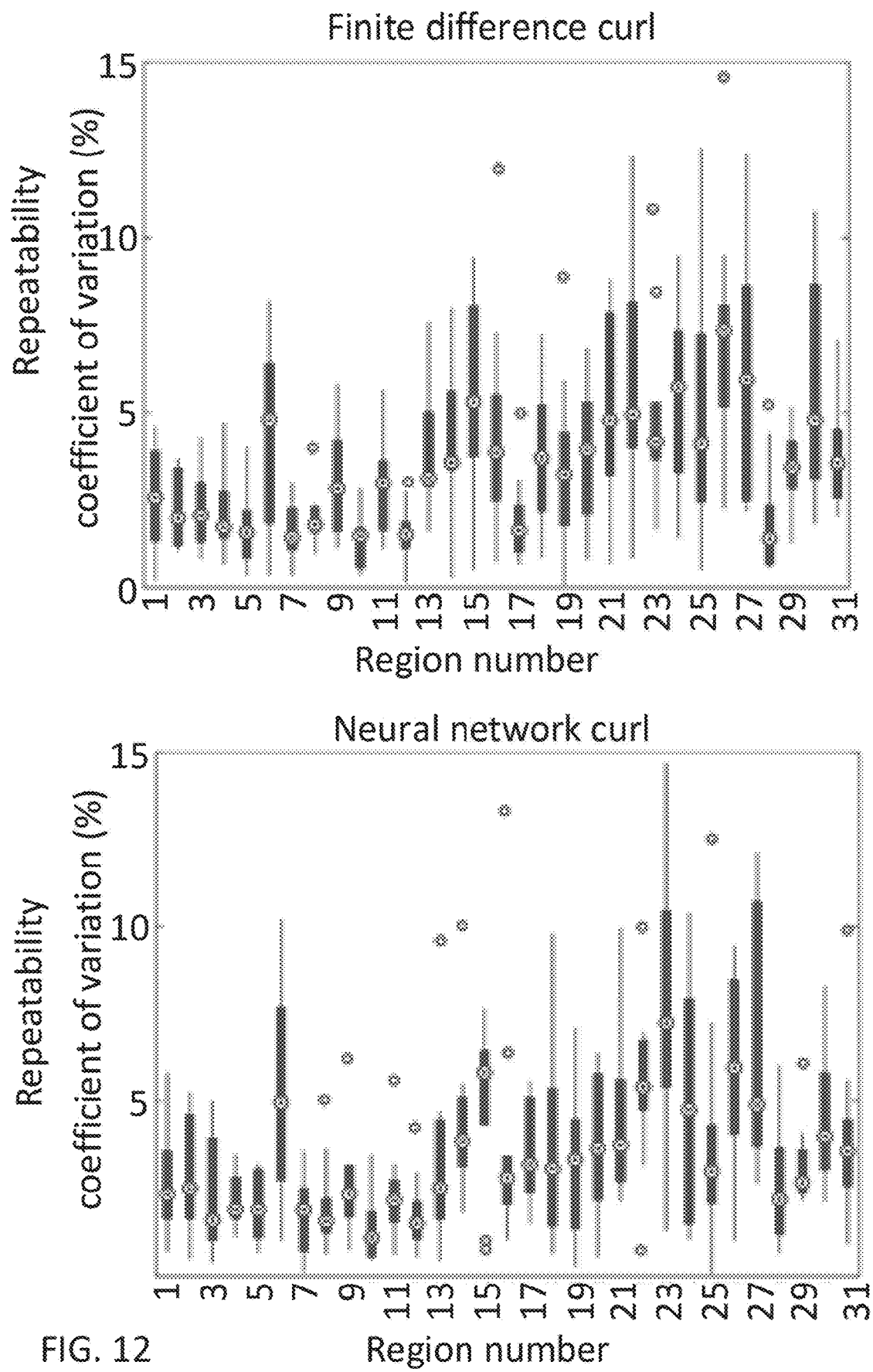
FIG. 12 shows examples of coefficient of variation values observed when calculating stiffness values from MRE data using conventional techniques for estimating derivatives on the left and when calculating stiffness values from MRE data using mechanisms described herein for estimating a derivative using a trained artificial neural network on the right.
Figure 13:
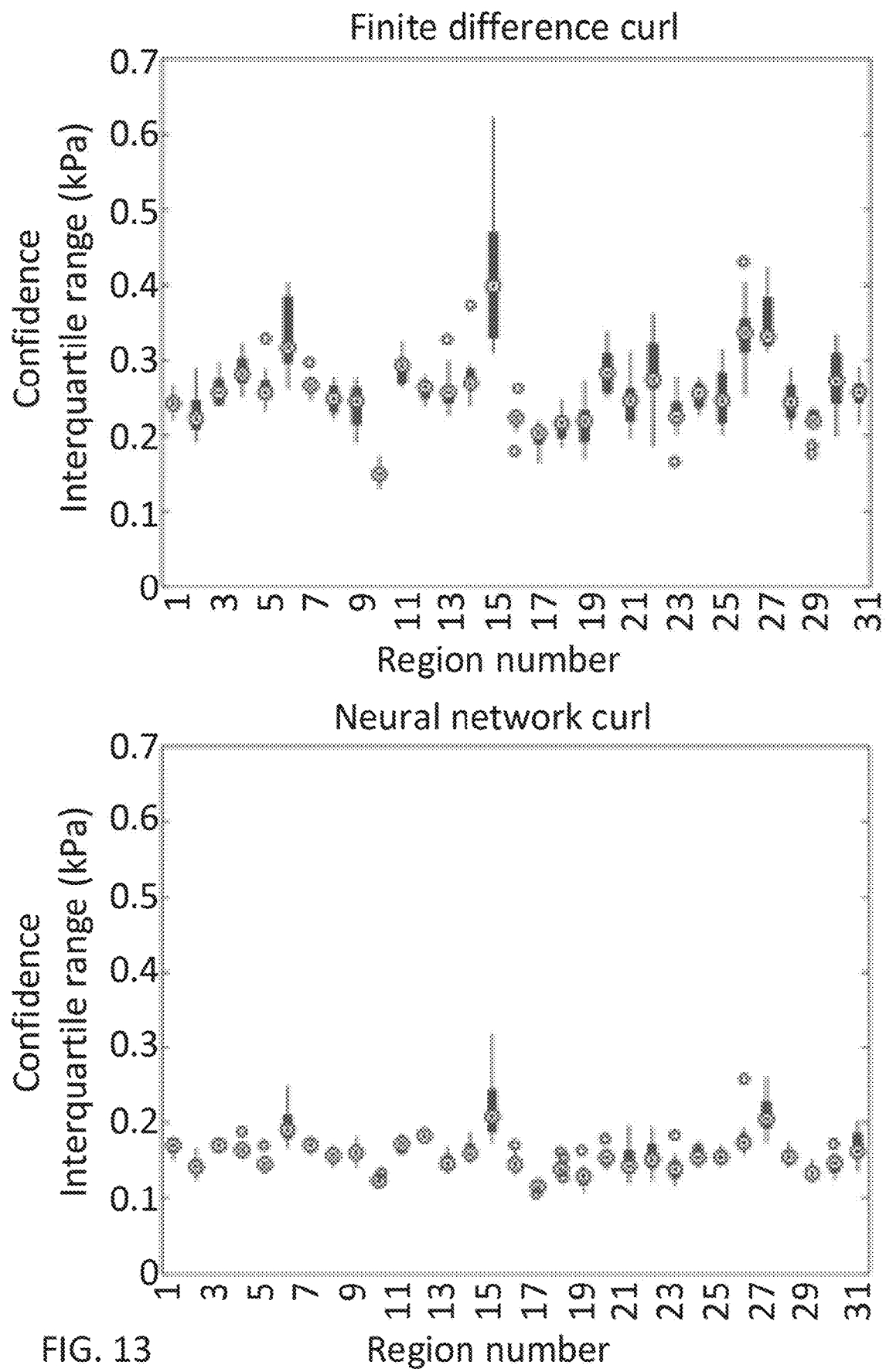
FIG. 13 shows examples of interquartile range values observed when calculating stiffness values from MRE data using conventional techniques for estimating derivatives on the left and when calculating stiffness values from MRE data using mechanisms described herein for estimating a derivative using a trained artificial neural network on the right.

FIGS. 12 and 13 show examples of coefficient of variation values and interquartile range, respectively, observed when calculating mechanical properties from MRE data using conventional techniques for estimating derivatives on the left and when calculating stiffness values from MRE data using mechanisms described herein for estimating a derivative using a trained artificial neural network on the right. Previously acquired brain MRE data (from 10 subjects with 3 repeat scans) was used to assess confidence and repeatability of mechanical property estimates derived from the derivative estimates. Mechanical property maps were computed using an edge-aware neural network inversion, and error maps were computed as the interquartile range (IQR) of the prediction interval using quantile regression (as described above in connection with FIG. 11). For each exam, mean mechanical property values and corresponding IQR were computed in 31 regions using a modified AAL atlas excluding regions with <10 voxels. From these summary data, the mean IQR across trials was computed to assess confidence and the coefficient of variation was computed to assess repeatability. Each box plot in FIGS. 12 and 13 shows the distribution over the 10 participants. Confidence in the stiffness estimates (computed as interquartile range of stiffness estimate by quantile regression) was significantly improved using the neural network version of the curl as illustrated in FIG. 13. Repeatability was not statistically different between the two techniques, as illustrated in FIG. 12.

Note that although the mechanisms described herein were generally described in the context of elastography, and in particular MRE, mechanisms described herein for estimating a derivative of a function represented in data that has a relatively low signal to noise ratio can be used in many applications. For example, the mechanisms described herein can be used in other MM areas, such as phase contrast flow, that utilize estimates of derivatives from MR data to analyze the data. As another example, mechanisms for estimating the derivative of a function represented in data that has a relatively low signal to noise ratio can be used in techniques for modeling prices of options contracts based on historical pricing data (e.g., stock price data). Additionally, although the mechanisms described herein were generally described in the context of estimating a derivative of a function represented in data that has a relatively low signal to noise ratio dues to the presence of noise and missing data points, the mechanisms described herein can also be used to estimate a derivative of a function represented in data that has a relatively low resolution (e.g., a low signal to noise ratio because of a lack of signal, rather than the presence of noise), such as relatively low spatial resolution (e.g., undersampled data, aliased data, etc.). In such a regime, conventional finite differences techniques can be heavily biased due to the limited sampling of the data, while the mechanisms described herein can provide more accurate estimates. For example, mechanisms for estimating the derivative of a function represented in data can be used in techniques for finite difference materials modeling based on relatively sparse data describing the properties of the materials.

Further Examples Having a Variety of Features

Example 1: A method for estimating a mechanical property based on a transformation of magnetic resonance elastography (MRE) data, comprising: receiving displacement data from an MRE data source, wherein the displacement data represents displacements of tissue in vivo; providing the displacement data to a trained artificial neural network (ANN), wherein the trained ANN was trained using a plurality of noisy input datasets as training data, each of the plurality of noisy input datasets corresponding to a function of a plurality of functions, and using one or more derivative datasets corresponding to the noisy input datasets to evaluate performance of the ANN during training, such that the trained ANN provides one or more output datasets corresponding to an analytical solution to a derivative of a function represented in an unlabeled input dataset thereby transforming the unlabeled input dataset into one or more derivatives of the unlabeled input dataset; receiving, from the trained ANN, an output dataset indicative of a derivative of the displacement data; and estimating stiffness of the tissue based on the derivative of the displacement data.

Example 2: The method of Example 1, wherein the plurality of functions are wave-like functions.

Example 3: The method of any one of Examples 1 or 2, wherein each of the plurality of functions includes no less than three independent variables.

Example 4: The method of any one of Examples 1 to 3, further comprising: receiving the plurality of functions; generating a plurality of input datasets using the plurality of functions, wherein each of the plurality of input datasets comprises a plurality of elements, each of the plurality of elements representing an output value of a particular function of the plurality of functions given a particular combination of input values; identifying, for each of the plurality of functions, at least one derivative; generating, for each of the plurality of functions, a derivative dataset using the at least one derivative, wherein the derivative dataset comprises a plurality of elements, each of the plurality of elements representing a value of the derivative of the function given a particular combination of input values; generating, for each of the plurality of input datasets, at least one noisy input dataset by adding an error term to at least a subset of the plurality of elements, such that the plurality of noisy input datasets is generated with each noisy input dataset corresponding to one of the plurality of functions and one or more of the derivative datasets; and training an ANN using the plurality of noisy input datasets as training data, and using the one or more derivative datasets corresponding to the noisy input datasets to evaluate performance of the artificial neural network during training, such that the trained ANN is generated Example 5: The method of Example 4, further comprising generating, for at least one of the plurality of input datasets, a first noisy input dataset by excluding at least a second subset of the plurality of elements such that the first noisy input dataset comprises fewer elements than the input dataset from which it was generated.

Example 6: The method of any one of Examples 1 to 5, wherein the derivative of the displacement data comprises a first partial derivative of the displacement data with respect to a first independent variable, the method further comprising: receiving, from the trained ANN, a second output dataset indicative of a second partial derivative of the displacement data with respect to a second independent variable; and estimating stiffness of the tissue based on the first partial derivative of the displacement data and the second partial derivative of the displacement data.

Example 7: The method of any one of any one of Examples 1 to 6, wherein the trained ANN comprises a convolutional neural network (CNN) that includes a plurality of filter modules, including a first filter module, a second filter module, and a third filter module, each having the same topology, wherein the first filter module is followed by a first batch normalization layer and a first rectified linear unit (ReLU) layer, an output of the first filter module is combined with an output of the second filter module via a residual connection followed by a second batch normalization layer and a second ReLU layer, and the output of the first filter module and the output of the second filter module is combined with an output of the third filter module via a second residual connection followed by a third batch normalization layer and a third ReLU layer, and wherein the ANN is configured to receive as input a 7×7×7×3 array of values representing a displacement field representing the displacement along each of three orthogonal coordinates across a 7×7×7 voxel block, and the ANN is configured to provide as an output three values, each of the values representing an estimate, at the central voxel of the 7×7×7 voxel block, of the partial derivative of the displacement field represented in the 7×7×7×3 along one of the three orthogonal coordinates.

Example 8: A system comprising: at least one hardware processor that is configured to: perform a method of any one of Examples 1 to 7.

Example 9: A non-transitory computer readable medium containing computer executable instructions that, when executed by a processor, cause the processor to perform a method of any one of Examples 1 to 7.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as RAM, Flash memory, electrically programmable read only memory (EPROM), electrically erasable programmable read only memory (EEPROM), etc.), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

It should be noted that, as used herein, the term mechanism can encompass hardware, software, firmware, or any suitable combination thereof.

It should be understood that the above described steps of the processes of FIG. 4 can be executed or performed in any order or sequence not limited to the order and sequence shown and described in the figures. Also, some of the above steps of the processes of FIG. 4 can be executed or performed substantially simultaneously where appropriate or in parallel to reduce latency and processing times.

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and rearranged in various ways.

What is claimed is:

1. A system for estimating a mechanical property based on a transformation of magnetic resonance elastography (MRE) data, the system comprising:
at least one hardware processor that is programmed to:
receive displacement data from an MRE data source, wherein the displacement data represents displacements of tissue in vivo;
provide the displacement data to a trained artificial neural network (ANN),
wherein the trained ANN was trained using a plurality of noisy input datasets as training data, each of the plurality of noisy input datasets corresponding to a function of a plurality of functions, and using one or more derivative datasets corresponding to the noisy input datasets to evaluate performance of the ANN during training, such that the trained ANN provides one or more output datasets corresponding to an analytical solution to a derivative of a function represented in an unlabeled input dataset thereby transforming the unlabeled input dataset into one or more derivatives of the unlabeled input dataset;
receive, from the trained ANN, an output dataset indicative of a derivative of the displacement data; and
estimate stiffness of the tissue based on the derivative of the displacement data.

2. The system of claim 1, wherein the plurality of functions are wave-like functions.

3. The system of claim 1, wherein each of the plurality of functions includes no less than three independent variables.

4. The system of claim 1, wherein the at least one hardware processor is further programmed to:
receive the plurality of functions;
generate a plurality of input datasets using the plurality of functions, wherein each of the plurality of input datasets comprises a plurality of elements, each of the plurality of elements representing an output value of a particular function of the plurality of functions given a particular combination of input values;
identify, for each of the plurality of functions, at least one derivative;
generate, for each of the plurality of functions, a derivative dataset using the at least one derivative, wherein the derivative dataset comprises a plurality of elements, each of the plurality of elements representing a value of the derivative of the function given a particular combination of input values;
generate, for each of the plurality of input datasets, at least one noisy input dataset by adding an error term to at least a subset of the plurality of elements, such that the plurality of noisy input datasets is generated with each noisy input dataset corresponding to one of the plurality of functions and one or more of the derivative datasets; and
train an ANN using the plurality of noisy input datasets as training data, and using the one or more derivative datasets corresponding to the noisy input datasets to evaluate performance of the artificial neural network during training, such that the trained ANN is generated.

5. The system of claim 4, wherein the at least one hardware processor is further programmed to generate, for at least one of the plurality of input datasets, a first noisy input dataset by excluding at least a second subset of the plurality of elements such that the first noisy input dataset comprises fewer elements than the input dataset from which it was generated.

6. The system of claim 1,
wherein the derivative of the displacement data comprises a first partial derivative of the displacement data with respect to a first independent variable, and
the at least one hardware processor is further programmed to:
receive, from the trained ANN, a second output dataset indicative of a second partial derivative of the displacement data with respect to a second independent variable; and
estimate stiffness of the tissue based on the first partial derivative of the displacement data and the second partial derivative of the displacement data.

7. The system of claim 1,
wherein the trained ANN comprises a convolutional neural network (CNN) that includes a plurality of filter modules, including a first filter module, a second filter module, and a third filter module, each having the same topology, wherein the first filter module is followed by a first batch normalization layer and a first rectified linear unit (ReLU) layer, an output of the first filter module is combined with an output of the second filter module via a residual connection followed by a second batch normalization layer and a second ReLU layer, and the output of the first filter module and the output of the second filter module is combined with an output of the third filter module via a second residual connection followed by a third batch normalization layer and a third ReLU layer, and wherein the ANN is configured to receive as input a 7×7×7×3 array of values representing a displacement field representing the displacement along each of three orthogonal coordinates across a 7×7×7 voxel block, and the ANN is configured to provide as an output three values, each of the values representing an estimate, at the central voxel of the 7×7×7 voxel block, of the partial derivative of the displacement field represented in the 7×7×7×3 along one of the three orthogonal coordinates.

8. A method for estimating a mechanical property based on a transformation of magnetic resonance elastography (MRE) data, comprising:

receiving displacement data from an MRE data source, wherein the displacement data represents displacements of tissue in vivo;

providing the displacement data to a trained artificial neural network (ANN),
wherein the trained ANN was trained using a plurality of noisy input datasets as training data, each of the plurality of noisy input datasets corresponding to a function of a plurality of functions, and using one or more derivative datasets corresponding to the noisy input datasets to evaluate performance of the ANN during training, such that the trained ANN provides one or more output datasets corresponding to an analytical solution to a derivative of a function represented in an unlabeled input dataset thereby transforming the unlabeled input dataset into one or more derivatives of the unlabeled input dataset;

receiving, from the trained ANN, an output dataset indicative of a derivative of the displacement data; and estimating stiffness of the tissue based on the derivative of the displacement data.

9. The method of claim 8, wherein the plurality of functions are wave-like functions.

10. The method of claim 8, wherein each of the plurality of functions includes no less than three independent variables.

11. The method of claim 8, further comprising:

receiving the plurality of functions;

generating a plurality of input datasets using the plurality of functions, wherein each of the plurality of input datasets comprises a plurality of elements, each of the plurality of elements representing an output value of a particular function of the plurality of functions given a particular combination of input values;

identifying, for each of the plurality of functions, at least one derivative;

generating, for each of the plurality of functions, a derivative dataset using the at least one derivative, wherein the derivative dataset comprises a plurality of elements, each of the plurality of elements representing a value of the derivative of the function given a particular combination of input values;

generating, for each of the plurality of input datasets, at least one noisy input dataset by adding an error term to at least a subset of the plurality of elements, such that the plurality of noisy input datasets is generated with each noisy input dataset corresponding to one of the plurality of functions and one or more of the derivative datasets; and training an ANN using the plurality of noisy input datasets as training data, and using the one or more derivative datasets corresponding to the noisy input datasets to evaluate performance of the artificial neural network during training, such that the trained ANN is generated.

12. The method of claim 11, further comprising generating, for at least one of the plurality of input datasets, a first noisy input dataset by excluding at least a second subset of the plurality of elements such that the first noisy input dataset comprises fewer elements than the input dataset from which it was generated.

13. The method of any claim 8,
wherein the derivative of the displacement data comprises a first partial derivative of the displacement data with respect to a first independent variable,
the method further comprising:
receiving, from the trained ANN, a second output dataset indicative of a second partial derivative of the displacement data with respect to a second independent variable; and
estimating stiffness of the tissue based on the first partial derivative of the displacement data and the second partial derivative of the displacement data.

14. The method of claim 8,
wherein the trained ANN comprises a convolutional neural network (CNN) that includes a plurality of filter modules, including a first filter module, a second filter module, and a third filter module, each having the same topology,
wherein the first filter module is followed by a first batch normalization layer and a first rectified linear unit (ReLU) layer, an output of the first filter module is combined with an output of the second filter module via a residual connection followed by a second batch normalization layer and a second ReLU layer, and the output of the first filter module and the output of the second filter module is combined with an output of the third filter module via a second residual connection followed by a third batch normalization layer and a third ReLU layer, and
wherein the ANN is configured to receive as input a 7×7×7×3 array of values representing a displacement field representing the displacement along each of three orthogonal coordinates across a 7×7×7 voxel block, and the ANN is configured to provide as an output three values, each of the values representing an estimate, at the central voxel of the 7×7×7 voxel block, of the partial derivative of the displacement field represented in the 7×7×7×3 along one of the three orthogonal coordinates.

15. A non-transitory computer readable medium containing computer executable instructions that, when executed by a processor, cause the processor to perform a method for estimating a mechanical property based on a transformation of magnetic resonance elastography (MRE) data, the method comprising:

receiving displacement data from an MRE data source, wherein the displacement data represents displacements of tissue in vivo;

providing the displacement data to a trained artificial neural network (ANN),
wherein the trained ANN was trained using a plurality of noisy input datasets as training data, each of the plurality of noisy input datasets corresponding to a function of a plurality of functions, and using one or more derivative datasets corresponding to the noisy input datasets to evaluate performance of the ANN during training, such that the trained ANN provides one or more output datasets corresponding to an analytical solution to a derivative of a function represented in an unlabeled input dataset thereby transforming the unlabeled input dataset into one or more derivatives of the unlabeled input dataset;
receiving, from the trained ANN, an output dataset indicative of a derivative of the displacement data; and
estimating stiffness of the tissue based on the derivative of the displacement data.

16. The non-transitory computer readable medium of claim 15, wherein the plurality of functions are wave-like functions.

17. The non-transitory computer readable medium of claim 15, wherein each of the plurality of functions includes no less than three independent variables.

18. The non-transitory computer readable medium of claim 15, wherein the method further comprises:
receiving the plurality of functions;
generating a plurality of input datasets using the plurality of functions, wherein each of the plurality of input datasets comprises a plurality of elements, each of the plurality of elements representing an output value of a particular function of the plurality of functions given a particular combination of input values;
identifying, for each of the plurality of functions, at least one derivative;
generating, for each of the plurality of functions, a derivative dataset using the at least one derivative, wherein the derivative dataset comprises a plurality of elements, each of the plurality of elements representing a value of the derivative of the function given a particular combination of input values;
generating, for each of the plurality of input datasets, at least one noisy input dataset by adding an error term to at least a subset of the plurality of elements, such that the plurality of noisy input datasets is generated with each noisy input dataset corresponding to one of the plurality of functions and one or more of the derivative datasets; and
training an ANN using the plurality of noisy input datasets as training data, and using the one or more derivative datasets corresponding to the noisy input datasets to evaluate performance of the artificial neural network during training, such that the trained ANN is generated.

19. The non-transitory computer readable medium of claim 18, wherein the method further comprises generating, for at least one of the plurality of input datasets, a first noisy input dataset by excluding at least a second subset of the plurality of elements such that the first noisy input dataset comprises fewer elements than the input dataset from which it was generated.

20. The non-transitory computer readable medium of claim 15,
wherein the derivative of the displacement data comprises a first partial derivative of the displacement data with respect to a first independent variable,
the method further comprising:
receiving, from the trained ANN, a second output dataset indicative of a second partial derivative of the displacement data with respect to a second independent variable; and
estimating stiffness of the tissue based on the first partial derivative of the displacement data and the second partial derivative of the displacement data.

21. The non-transitory computer readable medium of claim 15,
wherein the trained ANN comprises a convolutional neural network (CNN) that includes a plurality of filter modules, including a first filter module, a second filter module, and a third filter module, each having the same topology,
wherein the first filter module is followed by a first batch normalization layer and a first rectified linear unit (ReLU) layer, an output of the first filter module is combined with an output of the second filter module via a residual connection followed by a second batch normalization layer and a second ReLU layer, and the output of the first filter module and the output of the second filter module is combined with an output of the third filter module via a second residual connection followed by a third batch normalization layer and a third ReLU layer, and
wherein the ANN is configured to receive as input a 7×7×7×3 array of values representing a displacement field representing the displacement along each of three orthogonal coordinates across a 7×7×7 voxel block, and the ANN is configured to provide as an output three values, each of the values representing an estimate, at the central voxel of the 7×7×7 voxel block, of the partial derivative of the displacement field represented in the 7×7×7×3 along one of the three orthogonal coordinates.

* * * * *

UNITED STATES PATENT AND TRADEMARK OFFICE
CERTIFICATE OF CORRECTION

PATENT NO. : 12,019,133 B2
APPLICATION NO. : 17/796431
DATED : June 25, 2024
INVENTOR(S) : Matthew C. Murphy et al.

It is certified that error appears in the above-identified patent and that said Letters Patent is hereby corrected as shown below:

In the Specification

Column 9, Line 33, "MM" should be --MRI--.

Column 16, Line 27, "MM" should be --MRI--.

Column 21, Line 21, "MM" should be --MRI--.

Signed and Sealed this
Third Day of September, 2024

Katherine Kelly Vidal
*Director of the United States Patent and Trademark Office*